(12) United States Patent
Senoo et al.

(10) Patent No.: US 6,858,325 B2
(45) Date of Patent: Feb. 22, 2005

(54) ORGANIC COMPOUND AND ELECTROLUMINESCENT DEVICE USING THE SAME

(75) Inventors: Akihiro Senoo, Tokyo (JP); Yomishi Toshida, Yokohama (JP); Kazunori Ueno, Ebina (JP); Seiji Mashimo, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 121 days.

(21) Appl. No.: 10/266,602

(22) Filed: Oct. 9, 2002

(65) Prior Publication Data

US 2003/0157364 A1 Aug. 21, 2003

Related U.S. Application Data

(62) Division of application No. 09/078,570, filed on May 14, 1998, now Pat. No. 6,517,957.

(30) Foreign Application Priority Data

May 19, 1997 (JP) .............................................. 9-142958

(51) Int. Cl.$^7$ ........................ H05B 33/12; C07C 211/60
(52) U.S. Cl. ....................... 428/690; 428/917; 313/504; 313/506; 564/427
(58) Field of Search ................................ 428/690, 917; 313/504, 506; 564/427; 430/58.65, 58.75

(56) References Cited

U.S. PATENT DOCUMENTS

| | | | |
|---|---|---|---|
| 3,172,862 A | 3/1965 | Gurnee et al. | 252/301.3 |
| 3,173,050 A | 3/1965 | Gurnee | 313/108 |
| 3,710,167 A | 1/1973 | Dresner et al. | 313/108 A |
| 4,356,429 A | 10/1982 | Tang | 313/503 |
| 4,539,507 A | 9/1985 | VanSlyke et al. | 313/504 |
| 4,720,432 A | 1/1988 | VanSlyke et al. | 428/457 |
| 4,853,308 A | 8/1989 | Ong et al. | 430/59 |
| 5,118,986 A | 6/1992 | Ohnuma et al. | 313/504 |
| 5,759,444 A | 6/1998 | Enokida et al. | 252/301.16 |

FOREIGN PATENT DOCUMENTS

| | | |
|---|---|---|
| EP | 0 567 396 A1 | 10/1993 |
| JP | 59-194393 | 11/1984 |
| JP | 62-19876 | 1/1987 |
| JP | 63-264692 | 11/1988 |
| JP | 3-163188 | 7/1991 |
| JP | 5-25473 | 2/1993 |
| JP | 8-179526 | 7/1996 |
| JP | 62-19875 | 1/1997 |
| JP | 11-167992 | 6/1999 |

OTHER PUBLICATIONS

C.W. Tang et al., "Organic Electroluminescent Diodes," 51(12) *Appl. Phys. Lett.* 913–915 (Sep. 1987).
H.P. Schwob et al., "Charge transfer Exciton Fission in Anthracene Crystals," 58(4) *J. Chem. Phys.* 1542–1547 (Feb. 1973).
R.H. Partridge, "Electroluminescence from Polyvinylcarbazole Films: 3. Electroluminescent Devices," 24 *Polymer* 748–754 (Jun. 1983).
J. Kalinowski et al., "Magnetic Field Effects on Recombination Radiation in Tetracene Crystal," 36(3) *Chem. Phys. Lett.* 345–348 (Nov. 1975).
P.S. Vincett et al., "Electrical Conduction and Low Voltage Blue Electroluminescenc in Vacuum–Deposited Organic Films," 94 *Thin Solid Films* 171–183, (Aug. 1982).
M. Pope et al., "Electroluminescence in Organic Crystals," 38 *J. Chem. Phys.* 2042–2043 (1963), no month.
W. Helfrich et al., "Recombination radiation in Anthracene Crystals," 14(7) *Phys. Rev. Lett.* 229–231 (Feb. 1965).
W. Helfrich et al., "Transients of Volume–Controlled Current and of Recombination Radiation n Anthracene," 44(8) *J. Chem. Phys.* 2902–2909, (Apr. 1966).

*Primary Examiner*—Marie Yamnitzky
(74) *Attorney, Agent, or Firm*—Fitzpatrick, Cella, Harper & Scinto

(57) ABSTRACT

An electroluminescent device is formed of a pair of electrodes and an organic compound layer interposed between the electrodes. The organic compound layer is composed of an organic compound represented by the following general formula (1):

$$\begin{array}{c} Ar^3 \quad\quad Ar^4 \\ \diagdown \quad\quad \diagup \\ N-X-N \\ \diagup \quad\quad \diagdown \\ Ar^1 \quad\quad Ar^2 \end{array} \quad (1)$$

wherein X is a substituted or unsubstituted arylene group or a substituted or unsubstituted heterocyclic group, each of at least two groups among $Ar^1$, $Ar^2$, $Ar^3$, and $Ar^4$ is a substituted or unsubstituted fluorenyl group, and the remainder represents a substituted or unsubstituted aryl group.

4 Claims, 4 Drawing Sheets

ORGANIC COMPOUND AND ELECTROLUMINESCENT DEVICE USING THE SAME

This application is a division of U.S. application Ser. No. 09/078,570, filed May 14, 1998, now U.S. Pat. No. 6,517,957 B1.

BACKGROUND OF THE INVENTION

1. Field of the Invention

The present invention relates to a novel organic compound and an electroluminescent device using the same.

2. Description of the Related Art

Pope et al., first discovered an electroluminescence (EL) of an organic material, that is, single-crystal anthracene in 1963 (*J. Chem. Phys.,* 38, 2042 (1963)). Helfinch and Schneider succeeded in observing relatively strong EL in an injection EL material containing a solution system having a high injection efficiency in 1965 (*Phys. Rev. Lett.,* 14, 229 (1965)). Many studies of organic luminescent materials containing conjugated organic hosts and conjugated organic activators having fused benzene rings have been disclosed in U.S. Pat. Nos. 3,172,862, 3,173,050, and 3,710,167; *J. Chem. Phys.,* 44, 2902 (1966); *J. Chem. Phys.,* 58, 1542 (1973); and *Chem. Phys. Lett.,* 36, 345 (1975). Examples of disclosed organic hosts include naphthalene, anthracene, phenanthrene, tetracene, pyrene, benzpyrene, chrysene, picene, carbazole, fluorene, biphenyl, terphenyl, triphenylene oxide, dihalobiphenyls, trans-stilbene, and 1,4-diphenylbutadiene. Examples of disclosed activators include anthracene, tetracene and pentacene. Since these organic luminescent materials are provided as single layers having a thickness of more than 1 $\mu$m, a high electric field is required for luminescence. Under these circumferences, thin film devices formed by a vacuum evaporation process have been proposed (for example, *Thin Solid Films,* 94, 171 (1982); *Polymer,* 24, 748 (1983); and *J. Appl. Phys.,* 25, L773 (1986)). Although the thin film devices are effective for reducing the driving voltage, their luminance is far from a level for practical use.

Tang et al. developed an EL device having a high luminance for a low driving voltage (Appl. Phys. Lett., 51, 913 (1987) and U.S. Pat. No. 4,356,429). The EL device is fabricated by depositing two significantly thin layers, that is, a charge transport layer and a luminescent layer, between a positive electrode a negative electrode by a vacuum evaporation process. Such layered organic EL devices are disclosed in, for example, Japanese Patent Laid-Open Nos. 59-194393, 63-264692, and 3-163188, U.S. Pat. Nos. 4,539,507 and 4,720,432, and Appl. Phys. Lett., 55, 1467 (1989).

Also, an EL device of a triple-layered structure having independently a carrier transport function and a luminescent ability was disclosed in *Jpn. J. Appl. Phys.,* 27, L269 and L713 (1988). Since the carrier transportability is improved in such an EL device, the versatility of possible dyes in the luminescent layer is considerably increased. Further, the device configuration suggests the feasibility of improved luminescence by effectively trapping holes and electrons (or excimers) in the central luminescent layer.

Layered organic EL devices are generally formed by vacuum evaporation processes. EL devices having considerable luminance are also formed by casting processes (as described in, for example, Extended Abstracts (The 50th Autumn Meeting (1989), p. 1006 and The 51st Autumn Meeting (1990), p. 1041; The Japan Society of Applied Physics). Considerably high luminance is also achieved by a single-layered mixture-type EL device, in which the layer is formed by dip-coating a solution containing polyvinyl carbazole as a hole transport compound, an oxadiazole derivative as an electron transport compound and coumarin-6 as a luminescent material (as described in Extended Abstracts (The 38th Spring Meeting (1991), p. 1086; The Japan Society of Applied Physics and Related Societies).

As described above, the organic EL devices have been significantly improved and have suggested feasibility of a wide variety of applications; however, these EL devices have some problems for practical use, for example, insufficient luminance, a change in luminance during use for a long period, and deterioration by atmospheric gas containing oxygen and humidity. Further, wavelengths of electroluminescent light are limited, hence it is difficult to precisely determine hues of blue, green and red colors for use in full-color displays.

Japanese Patent Laid-Open No. 5-25473 discloses an electroluminescent device using an organic compound represented by the following general formula (A) as a hole transfer material:

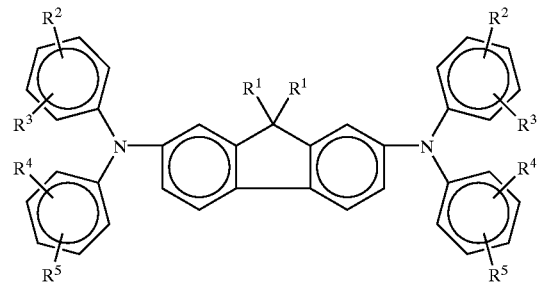

(A)

wherein $R^1$ is an alkyl or aralkyl group, and $R^2$, $R^3$, $R^4$ and $R^5$ are each a hydrogen or halogen atom or an alkyl or alkoxyl group. The organic compound is capable of forming an EL device which can drive at a low voltage and which has high luminance and high durability.

According to the results by the present inventors, however, a light emitting diode (LED) and a display using such an EL device are inevitably heated during operation. Since organic compounds represented by the formula (A) have a relatively low melting temperature and a glass transition temperature, their durability is insufficient due to deterioration by heat.

SUMMARY OF THE INVENTION

It is an object of the present invention to provide a novel organic compound in achieving an electroluminescent device with high luminance and high durability.

It is another object of the present invention to provide an electroluminescent device showing versatility of wavelengths of luminescent light and high durability.

It is a further object of the present invention to provide an electroluminescent device emitting light with high luminance.

An aspect of the present invention is an organic compound represented by the following general formula (1):

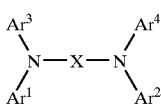

(1)

wherein X is a substituted or unsubstituted arylene group or a substituted or unsubstituted heterocyclic group, each of at least two groups among $Ar^1$, $Ar^2$, $Ar^3$, and $Ar^4$ is a substituted or unsubstituted fluorenyl group, and the remainder represents a substituted or unsubstituted aryl group.

Another aspect of the present invention is an electroluminescent device comprising a pair of electrodes and an organic compound layer interposed between said electrodes, said organic compound layer comprising an organic compound represented by the following general formula (1):

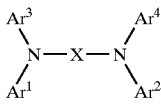

(1)

wherein X is a substituted or unsubstituted arylene group or a substituted or unsubstituted heterocyclic group, each of at least two groups among $Ar^1$, $Ar^2$, $Ar^3$, and $Ar^4$ is a substituted or unsubstituted fluorenyl group, and the remainder represents a substituted or unsubstituted aryl group.

The electroluminescent device in accordance with the present invention can emit a variety of hues and has high durability. Further, the electroluminescent device has high luminance.

DESCRIPTION OF THE PREFERRED EMBODIMENT

Figure 1:
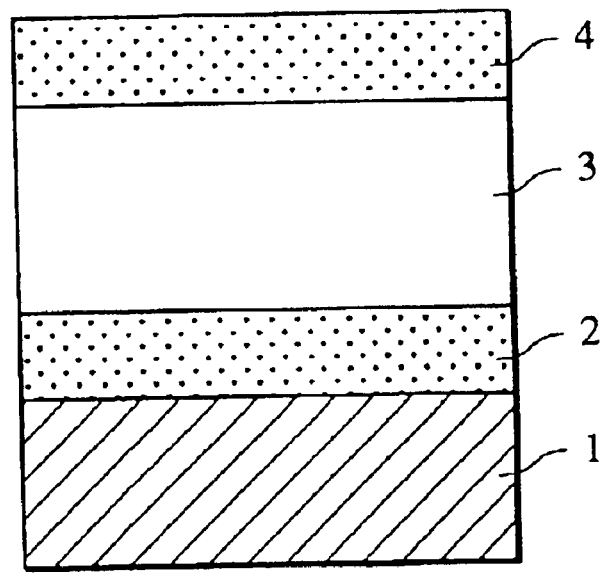
FIG. 1 is a schematic cross-sectional view of an embodiment of an electroluminescent device in accordance with the present invention.

The organic compound in accordance with the present invention is represented by the following general formula (1):

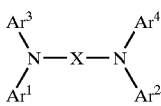

(1)

In the formula (1), X is a substituted or unsubstituted arylene group or a heterocyclic group, each of at least two groups among $Ar^1$, $Ar^2$, $Ar^3$, and $Ar^4$ is a substituted or unsubstituted fluorenyl group, and the remainder represents a substituted or unsubstituted aryl group.

Three or all of $Ar^1$, $Ar^2$, $Ar^3$, and $Ar^4$ may be substituted or unsubstituted fluorenyl groups. When some of $Ar^1$, $Ar^2$, $Ar^3$, and $Ar^4$ are not substituted or unsubstituted fluorenyl groups, these must be substituted or unsubstituted aryl groups.

When two groups among $Ar^1$, $Ar^2$, $Ar^3$, and $Ar^4$ are substituted or unsubstituted fluorenyl groups, there are three configurations of the substituted or unsubstituted fluorenyl groups in the organic compound as follows:

A. Either $Ar^1$ or $Ar^3$, and either $Ar^2$ or $Ar^4$
B. $Ar^1$ and $Ar^3$
C. $Ar^2$ and $Ar^4$ When three groups among $Ar^1$, $Ar^2$, $Ar^3$, and $Ar^4$ are substituted or unsubstituted fluorenyl groups, there are two configurations of the substituted or unsubstituted fluorenyl groups in the organic compound as follows:

D. Either $Ar^1$ or $Ar^3$, $Ar^2$ and $Ar^4$
E. Either $Ar^2$ or $Ar^4$, $Ar^1$ and $Ar^3$ When $Ar^3$ and $Ar^4$ in the formula (1) are substituted or unsubstituted fluorenyl groups, the organic compounds in accordance with the present invention are represented by the formula (4):

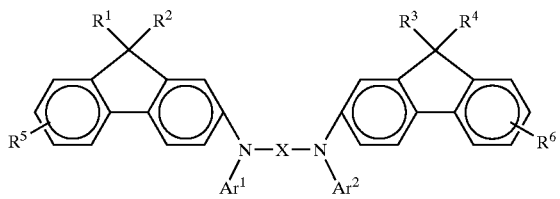

(4)

wherein X is a substituted or unsubstituted arylene group or a substituted or unsubstituted heterocyclic group; $Ar^1$ and $Ar^2$ are each a substituted or unsubstituted aryl group; $R^1$, $R^2$, $R^3$ and $R^4$ are each independently a hydrogen or halogen atom, or a substituted or unsubstituted alkyl, alkoxyl, or aryl group; and $R^5$ and $R^6$ are each independently a hydrogen or halogen atom, a nitro or cyano group, or a substituted or unsubstituted alkyl, alkoxyl, aryl, amino or carbonyl group.

Examples of the substituted or unsubstituted arylene group include phenylene, biphenylene, terphenylene, naphthylene, fluorenylene, pyrenylene, and stilbene groups.

Examples of the unsubstituted heterocyclic groups include divalent moieties of the following compounds, e.g. carbazole, dibenzofuran, dibenzothiophene, fluorenon, oxazole, oxadiazole, and thiadiazole. Examples of the substituent groups in the substituted arylene groups and the substituted heterocyclic groups include halogen atoms, e.g. fluorine, chlorine, bromine, and iodine; alkyl groups, e.g. methyl and ethyl, n-propyl, and iso-propyl groups; alkoxyl groups, e.g. methoxy, ethoxy, and phenoxy groups; aralkyl groups, e.g. benzyl, phenethyl, and propylphenyl groups; a nitro group; a cyano group; substituted amino groups, e.g. dimethylamino, dibenzylamino, diphenylamino, and morpholino groups; aryl groups, e.g. phenyl, tolyl, biphenyl, naphthyl, anthryl, and pyrenyl groups; and heterocyclic groups, e.g. pyridyl, thienyl, furyl, quinolyl, and carbazolyl groups.

In the formula (4), each of $Ar^1$ and $Ar^2$ is a substituted or unsubstituted aryl group. Examples of substituted or unsubstituted aryl groups include phenyl groups, and polycyclic or heterocyclic groups, e.g. biphenyl, terphenyl, naphthyl, anthryl, and pyrenyl groups. Examples of the substituent groups in the substituted aryl groups are the same as above.

Each of $R^1$, $R^2$, $R^3$ and $R^4$ is independently a hydrogen or halogen atom, or a substituted or unsubstituted alkyl, alkoxyl, or aryl group. Examples of the alkyl groups include methyl, ethyl, n-propyl, and iso-propyl; examples of the alkoxyl groups include methoxy, ethoxy, and phenoxy groups; and examples of the aryl groups include phenyl, biphenyl, and naphthyl groups. Examples of the substituent groups in these substituted groups are the same as above.

Each of $R^5$ and $R^6$ is independently a hydrogen or halogen atom, a nitro or cyano group, or a substituted or unsubstituted alkyl, alkoxyl, aryl, amino or carbonyl group. Examples of the alkyl groups include methyl, ethyl, n-propyl, and iso-propyl; examples of the alkoxyl groups include methoxy, ethoxy, and phenoxy groups; examples of the aryl groups include phenyl, biphenyl, and naphthyl groups; examples of the amino groups include dimethyl amino and diphenyl amino groups; and examples of the carbonyl groups include methylcarbonyl, phenylcarbonyl, and cyclohexylcarbonyl groups. Examples of the substituent groups in these substituted groups are the same as above.

The compound represented by the formula (4) corresponds to the above-mentioned configuration A when two groups among $Ar^1$, $Ar^2$, $Ar^3$ and $Ar^4$ in the formula (1) are substituted. The above description is also applicable to the configurations B and C.

When all of $Ar^1$, $Ar^2$, $Ar^3$ and $Ar^4$ in the formula (1) are substituted or unsubstituted fluorenyl groups, the organic compounds in accordance with the present invention are represented by the formula (5):

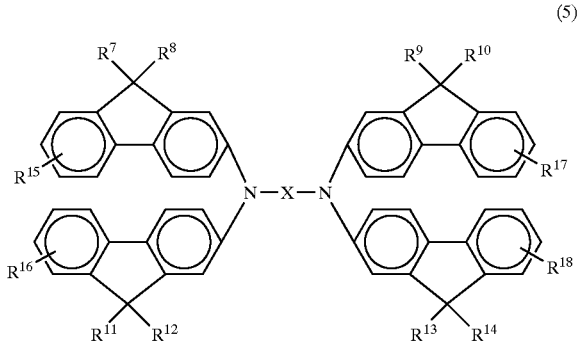

(5)

wherein X is a substituted or unsubstituted arylene group or a substituted or unsubstituted heterocyclic group, and examples of such groups are the same as above. In the formula (5), $R^7$, $R^8$, $R^9$, $R^{10}$, $R^{11}$, $R^{12}$, $R^{13}$, and $R^{14}$ are each independently a hydrogen or halogen atom, or a substituted or unsubstituted alkyl, alkoxyl, or aryl group, and examples of such atoms and groups are the same as in $R^1$, $R^2$, $R^3$, and $R^4$. Each of $R^{15}$, $R^{16}$, $R^{17}$, and $R^{18}$ is independently a hydrogen or halogen atom, a nitro or cyano group, or a substituted or unsubstituted alkyl, alkoxyl, aryl, amino or carbonyl group, and examples of such atoms and groups are the same as in $R^5$ and $R^6$.

The above description regarding the formulae (4) and (5) is also applicable to the above-mentioned configurations D and E when three among $Ar^1$, $Ar^2$, $Ar^3$ and $Ar^4$ are substituted or unsubstituted fluorenyl groups.

An organic compound represented by the formula (1) is synthesized by reaction of an iodine compound with an amine compound. The reaction is preferably performed in the presence of a metallic catalyst, for example, a copper catalyst.

The synthetic procedure is as follows. A compound represented by the formula (2) is allowed to react with a compound represented by the formula (3):

(2)

wherein X is a substituted or unsubstituted arylene group, or a substituted or unsubstituted heterocyclic group;

(3)

wherein Ar and Ar' are each a substituted or unsubstituted fluorenyl group or a substituted or unsubstituted aryl group. The organic compound represented by the general formula (1) is thereby prepared:

(1)

wherein each of at least two groups among $Ar^1$, $Ar^2$, $Ar^3$, and $Ar^4$ is a substituted or unsubstituted fluorenyl group, and the remainder represents a substituted or unsubstituted aryl group.

Examples of the organic compounds represented by the formula (1) will be described below without limiting the scope of the present invention.

Compound 1

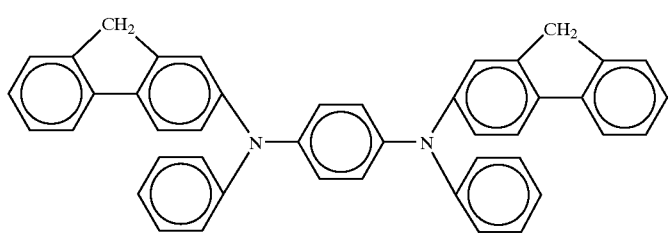

-continued
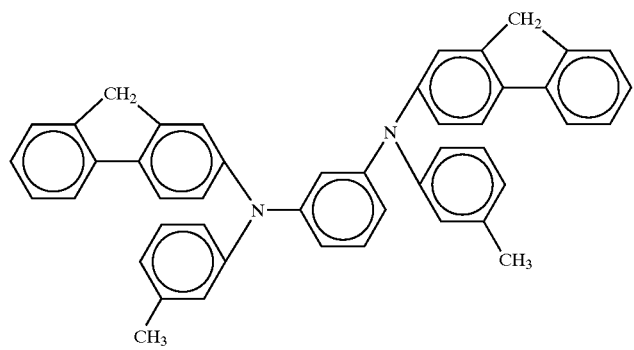
Compound 2
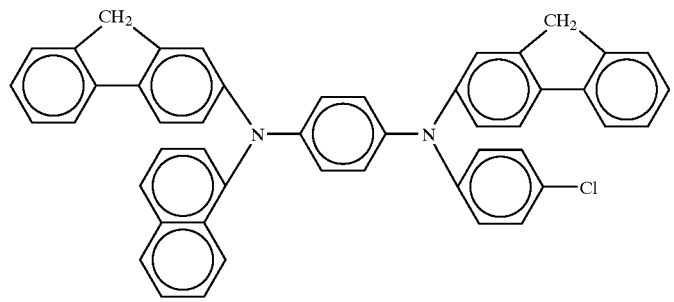
Compound 3
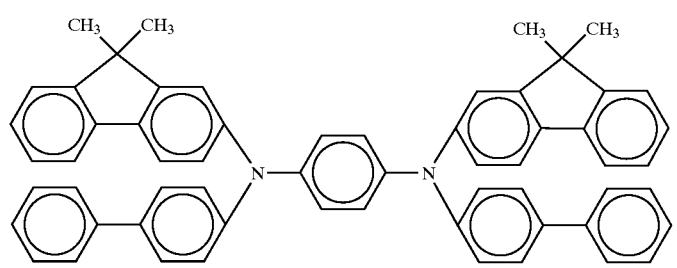
Compound 4
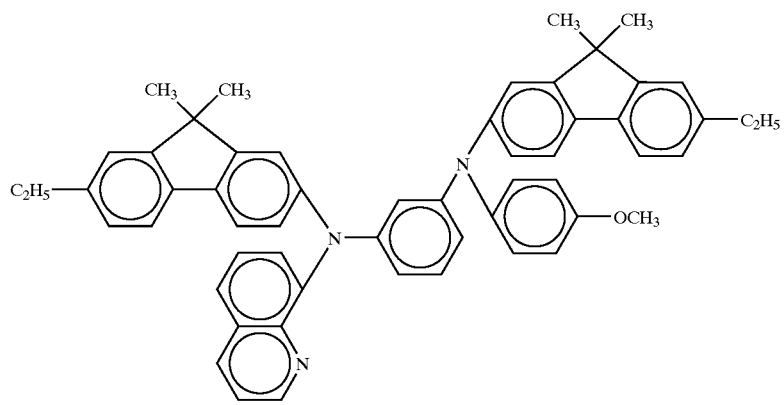
Compound 5

-continued
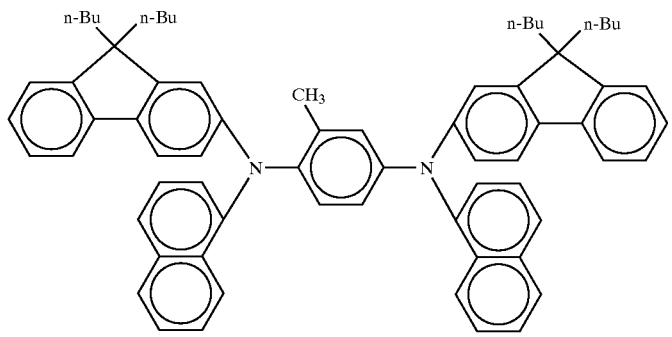
Compound 6
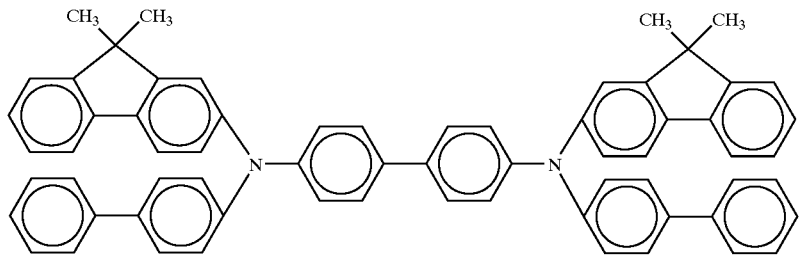
Compound 7
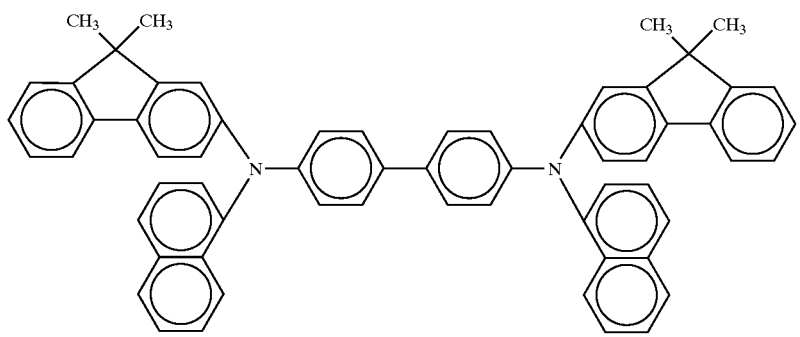
Compound 8
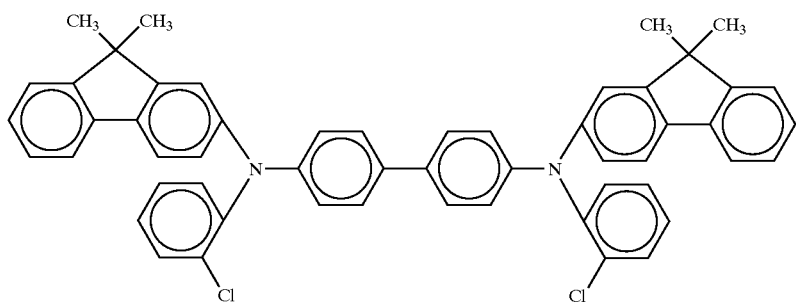
Compound 9
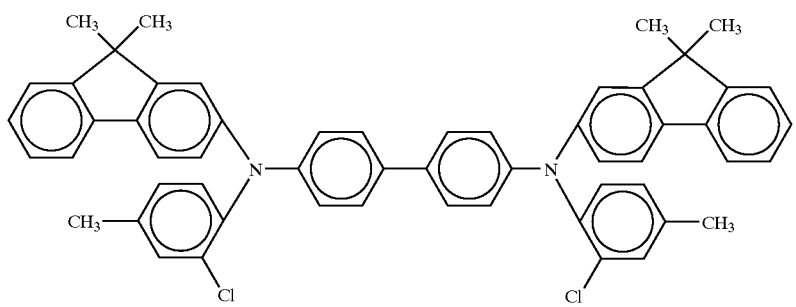
Compound 10

-continued
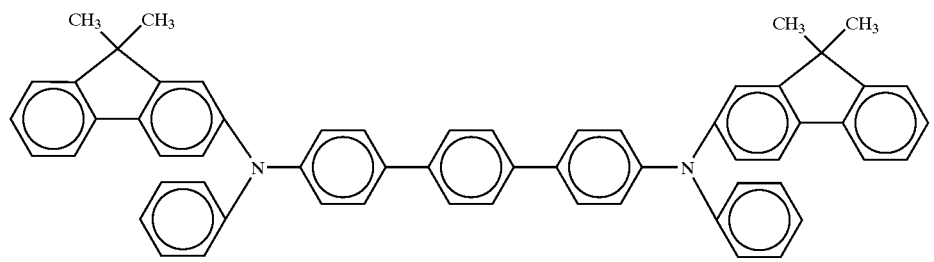
Compound 11
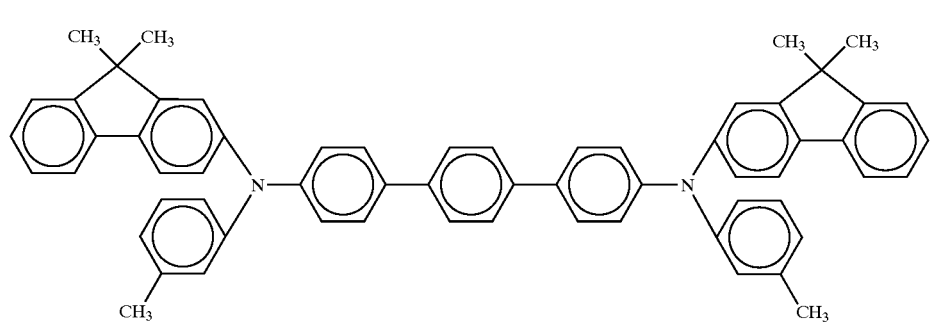
Compound 12
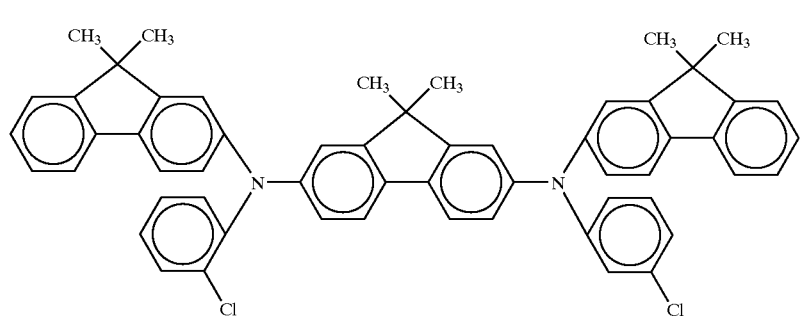
Compound 14
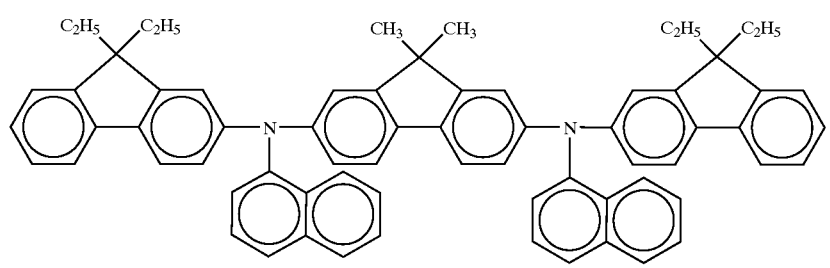
Compound 15
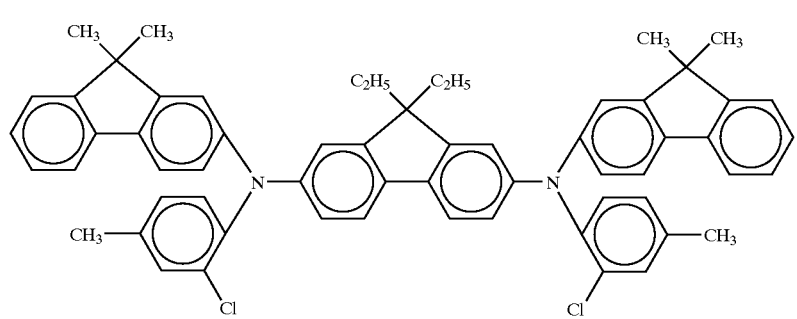
Compound 16

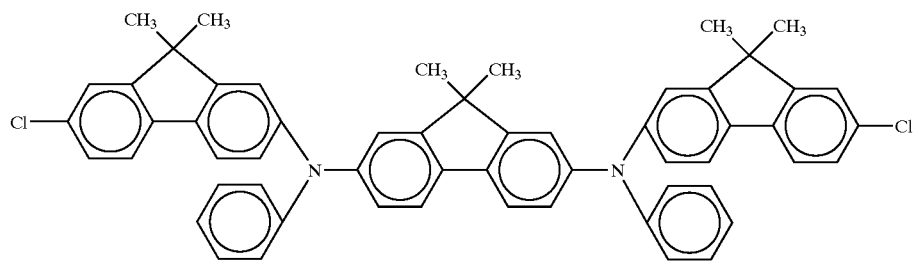
Compound 17
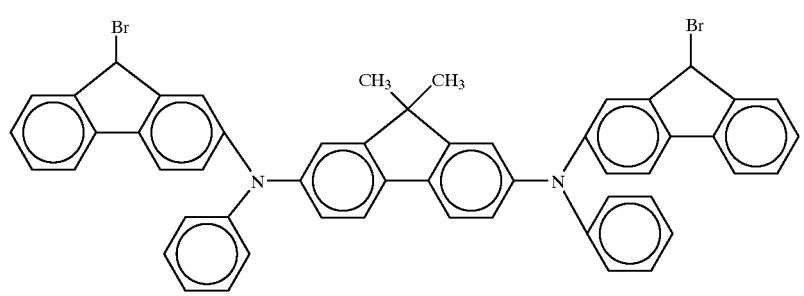
Compound 18
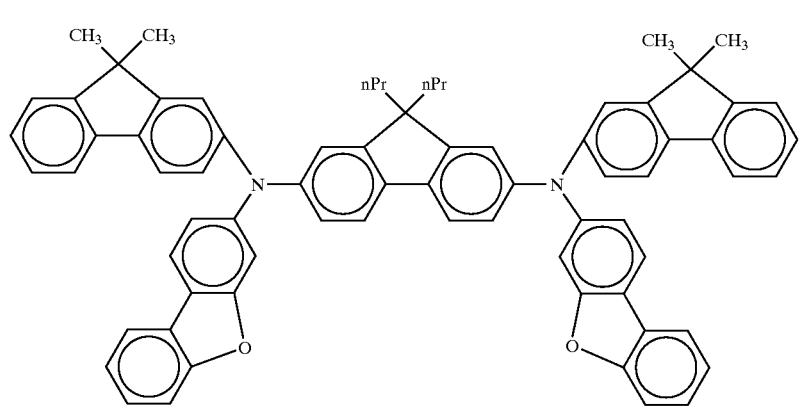
Compound 19
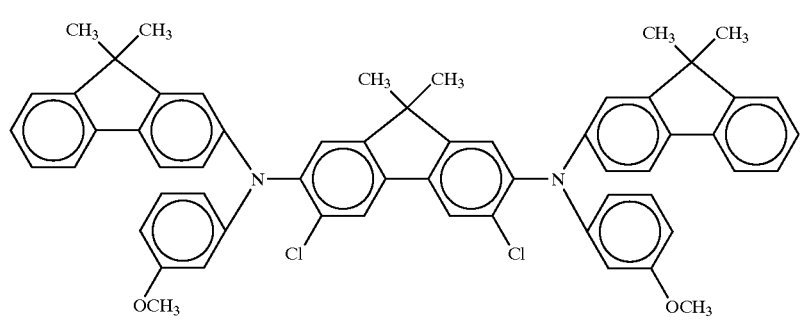
Compound 20
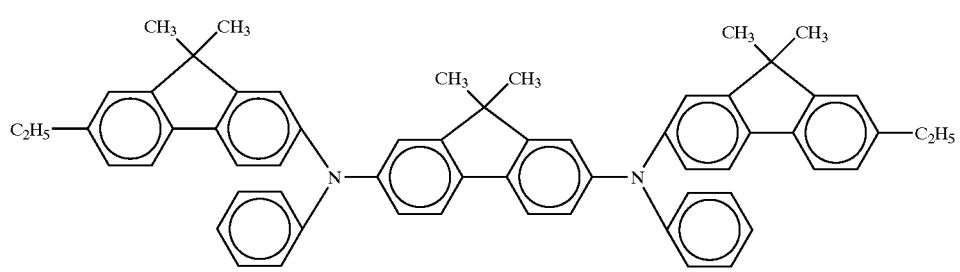
Compound 21

-continued
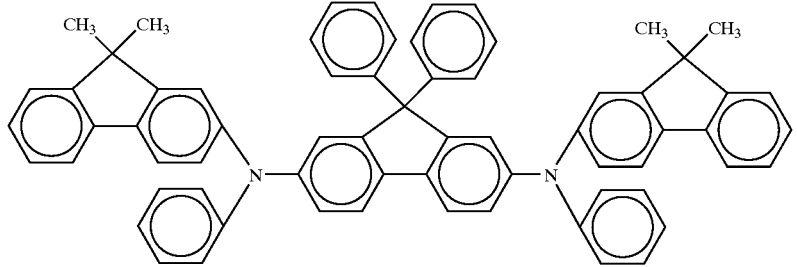
Compound 22
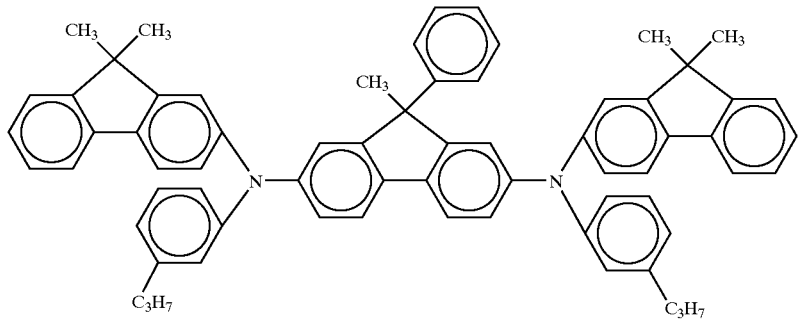
Compound 23
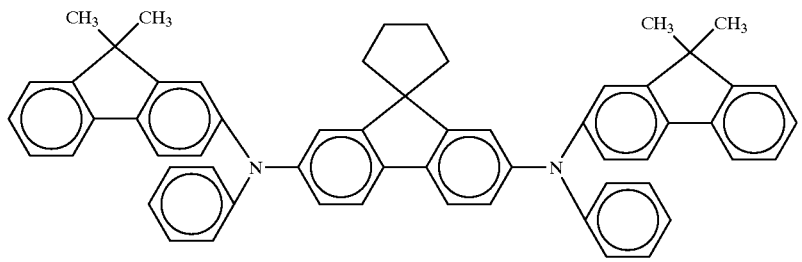
Compound 24
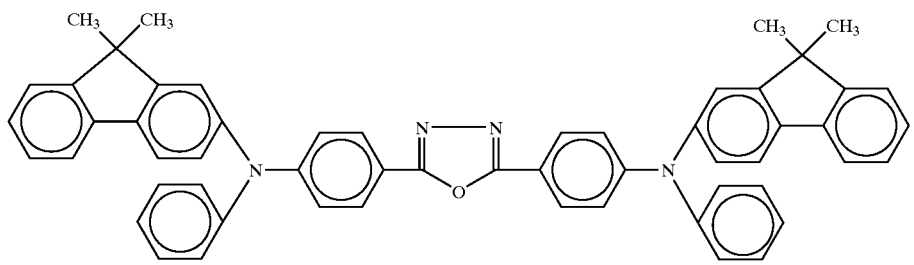
Compound 25
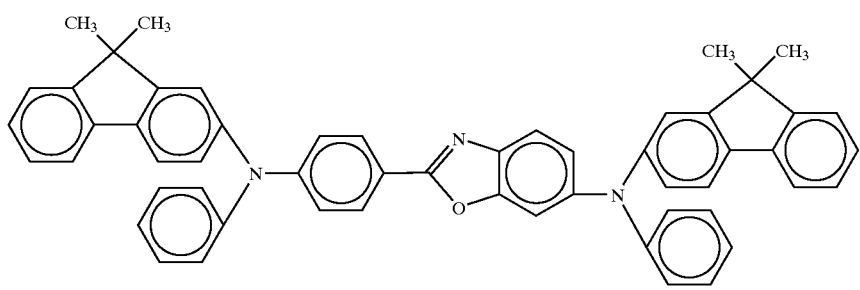
Compound 26

-continued
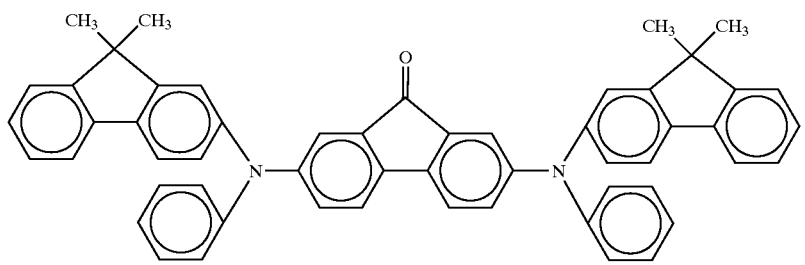
Compound 27
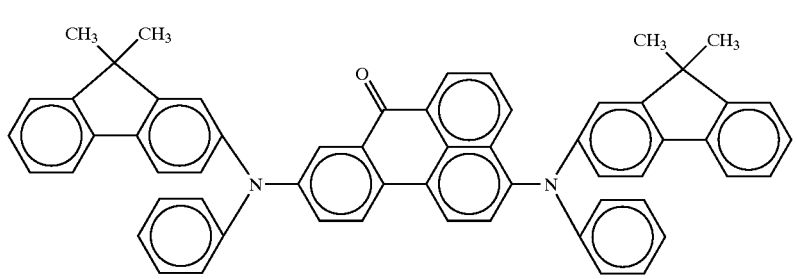
Compound 28
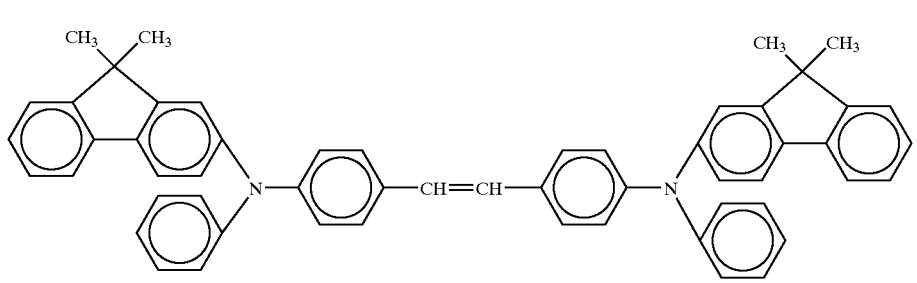
Compound 29
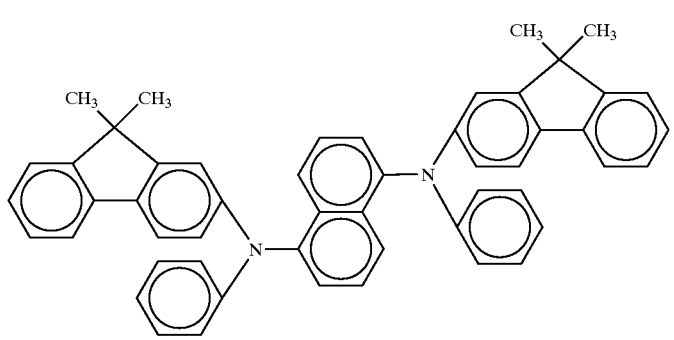
Compound 30
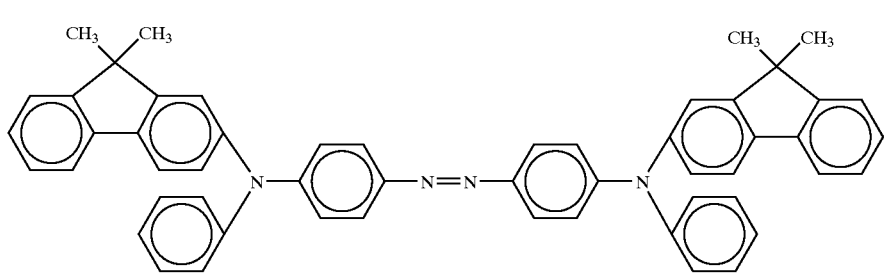
Compound 31

-continued
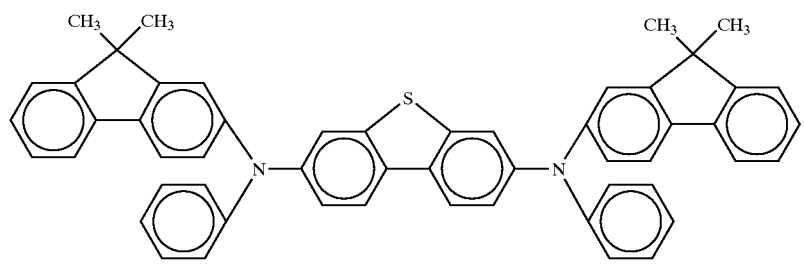
Compound 32
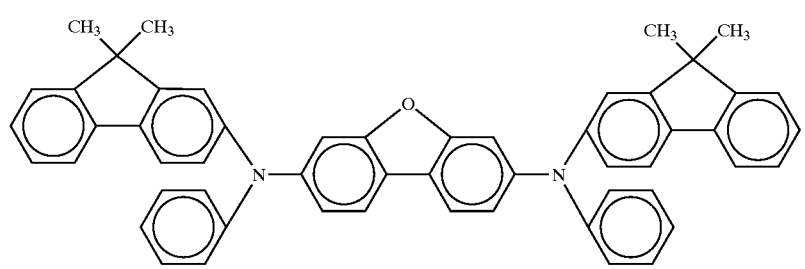
Compound 33
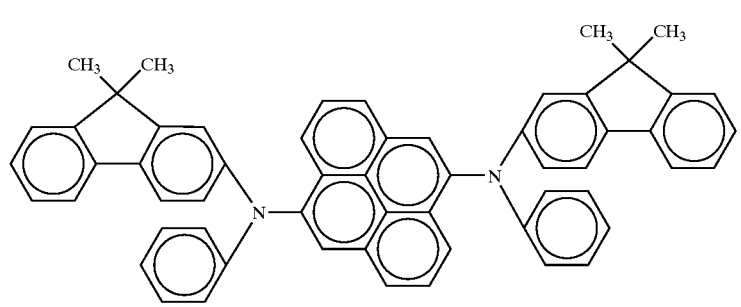
Compound 34
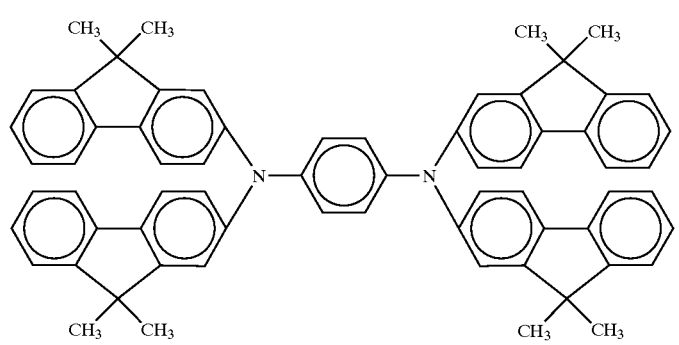
Compound 35
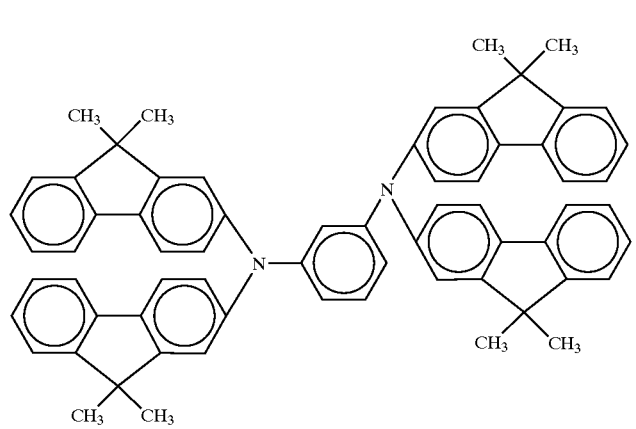
Compound 36

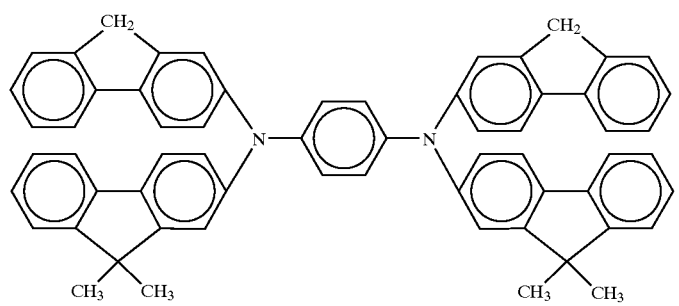
Compound 37
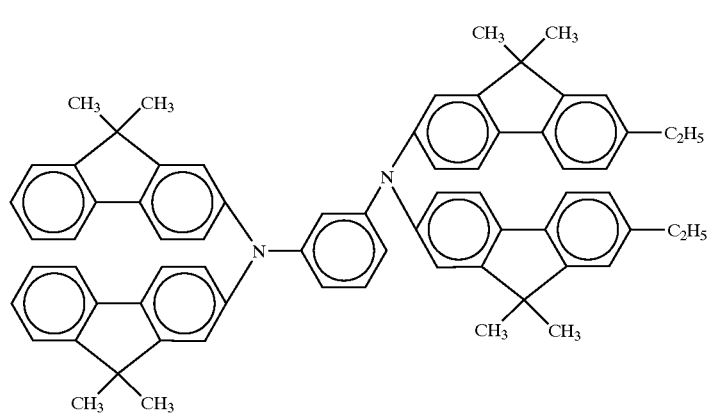
Compound 38
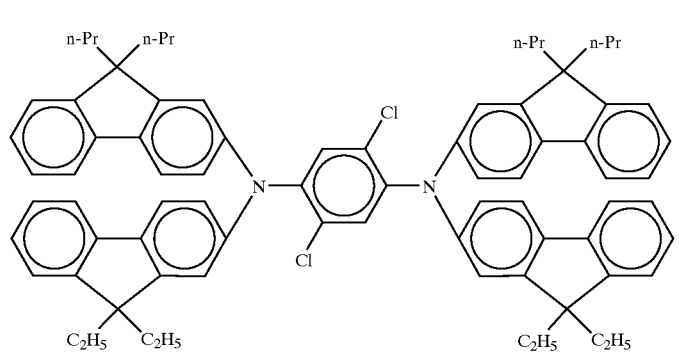
Compound 39
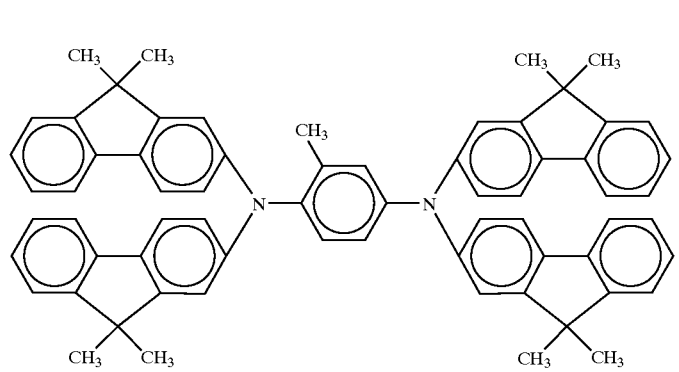
Compound 40

-continued
Compound 41
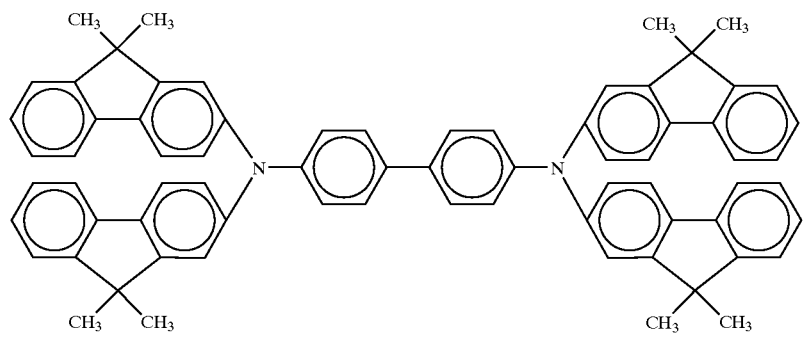
Compound 42
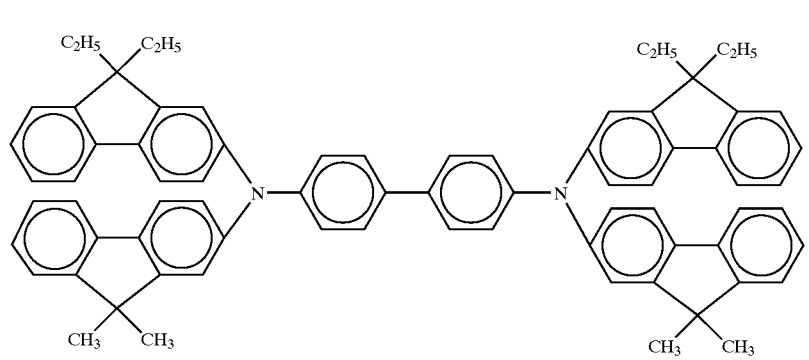
Compound 43
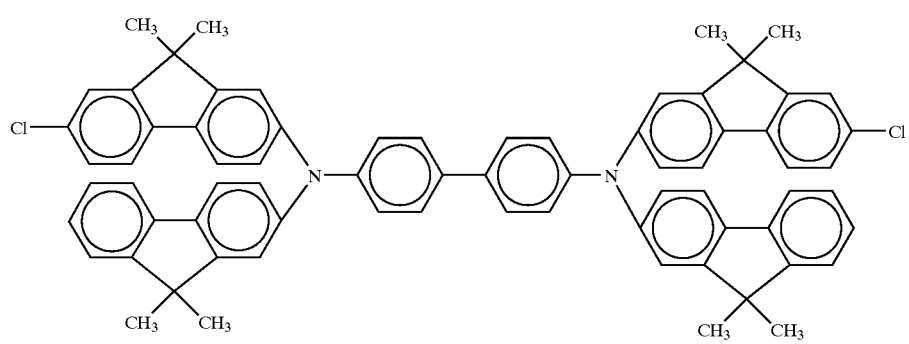
Compound 44
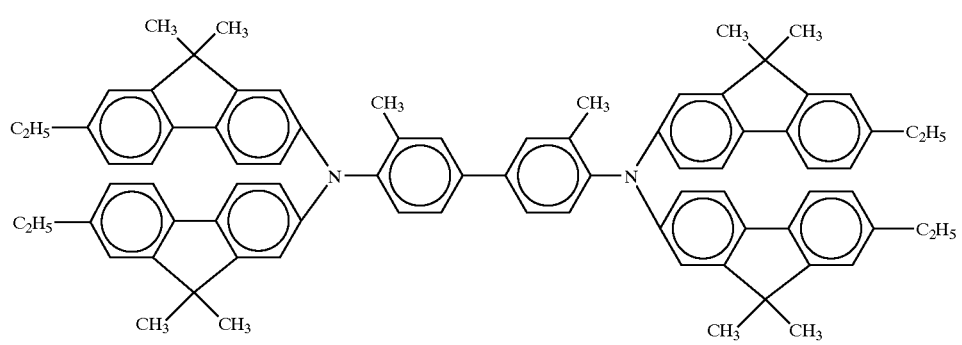
Compound 45
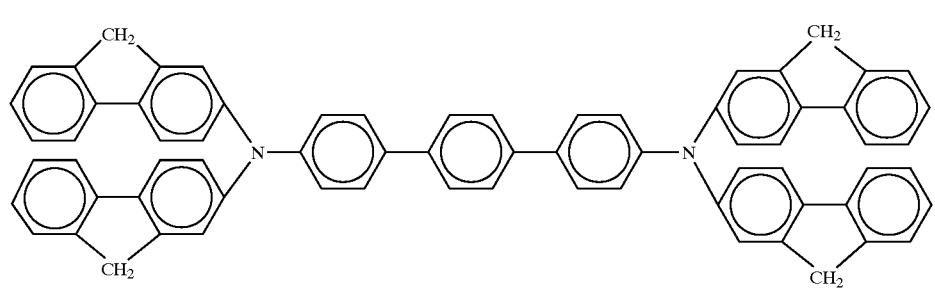

-continued
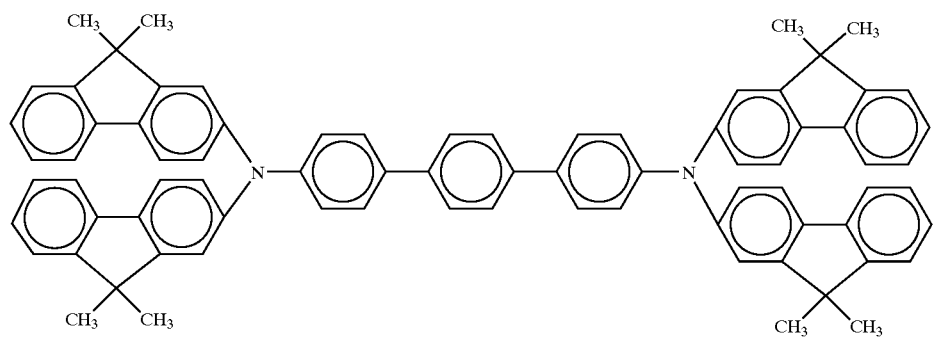
Compound 46
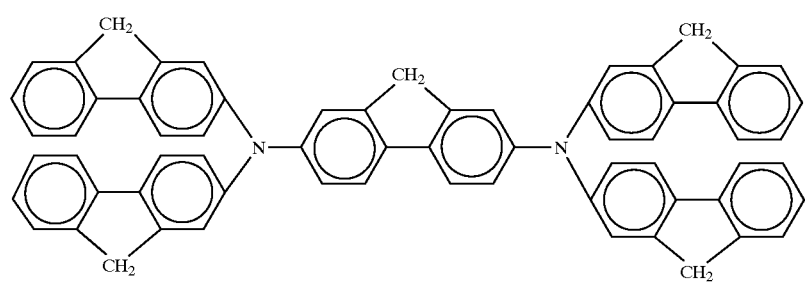
Compound 47
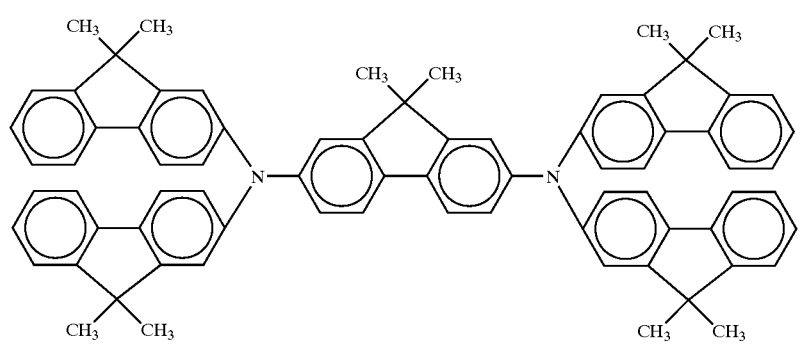
Compound 48
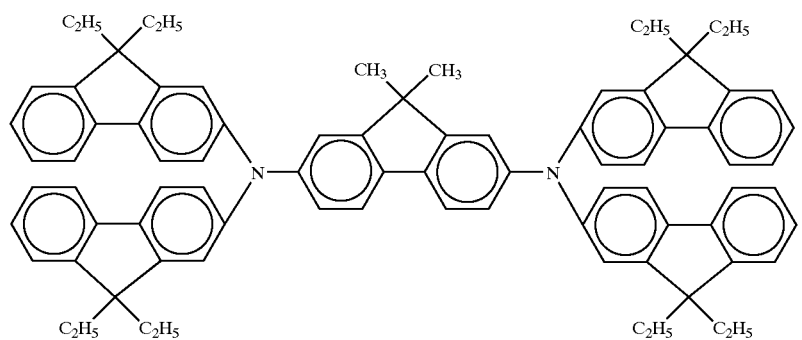
Compound 49
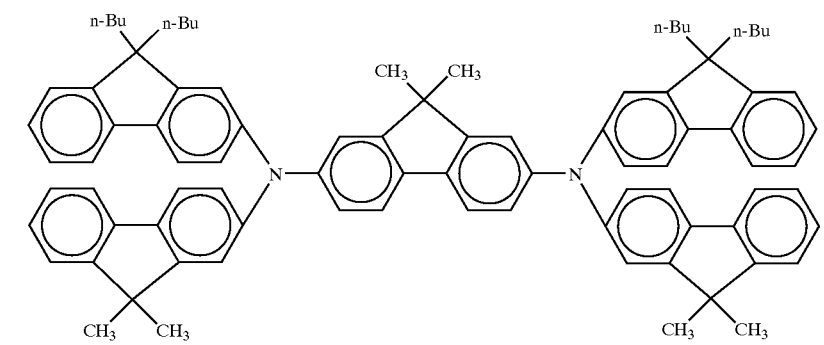
Compound 50

Compound 51
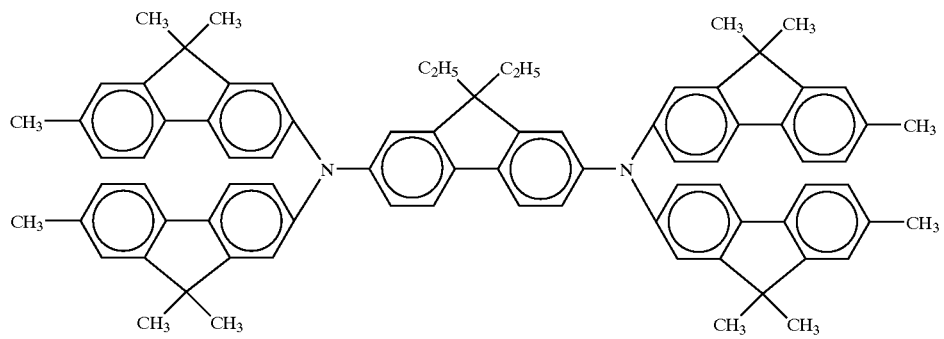
Compound 52
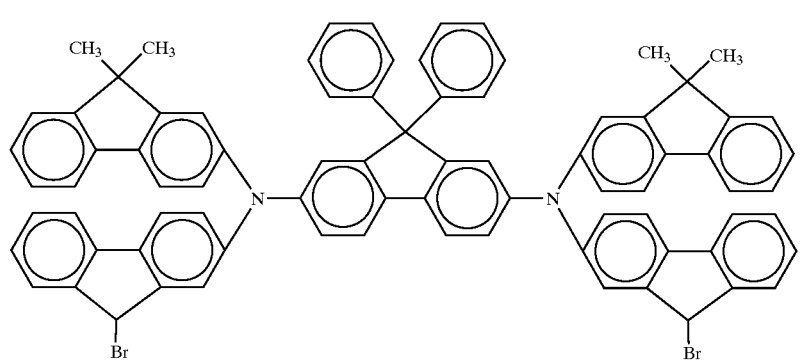
Compound 53
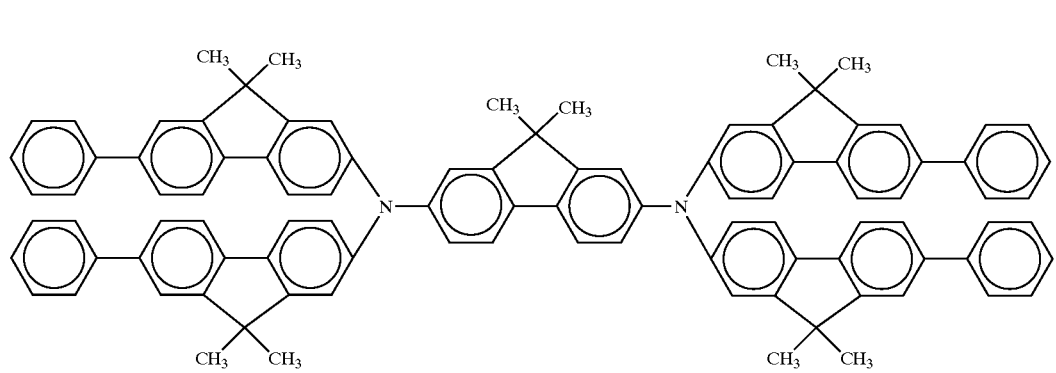
Compound 54
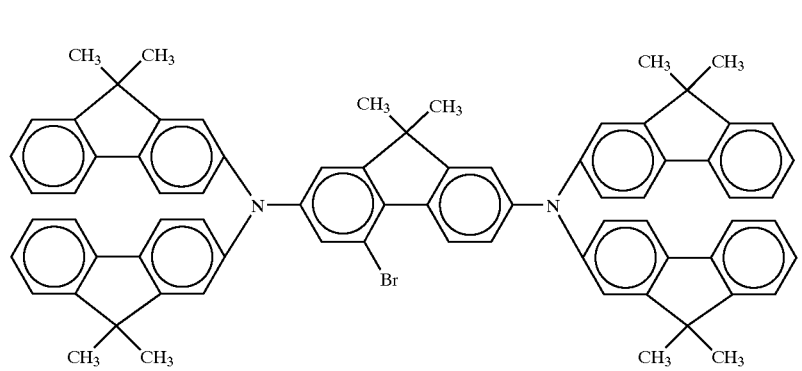

-continued
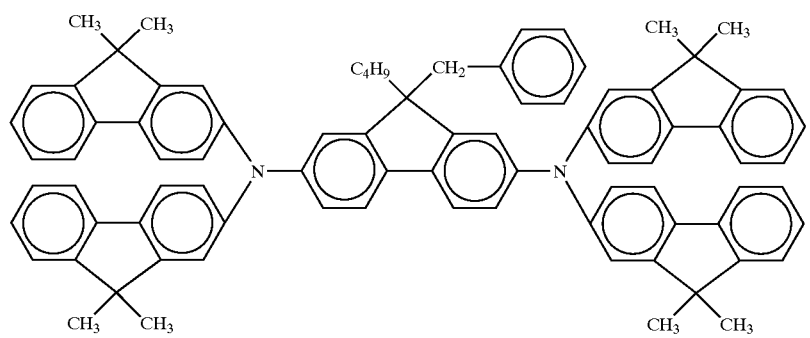
Compound 55
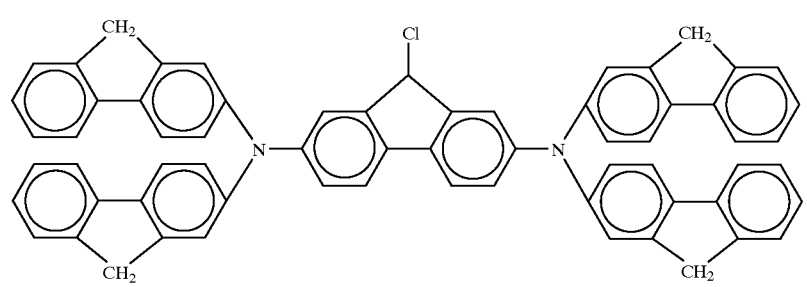
Compound 56
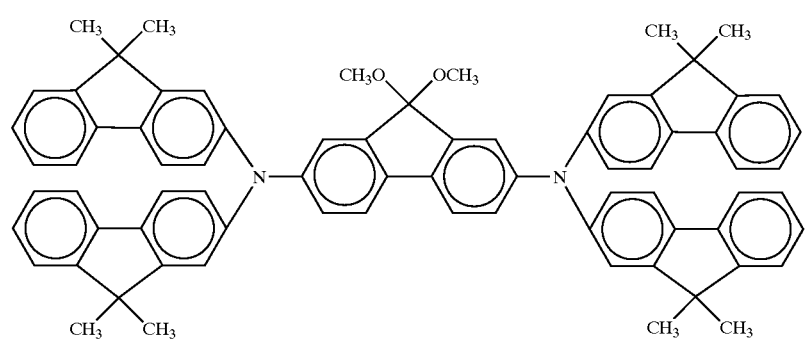
Compound 57
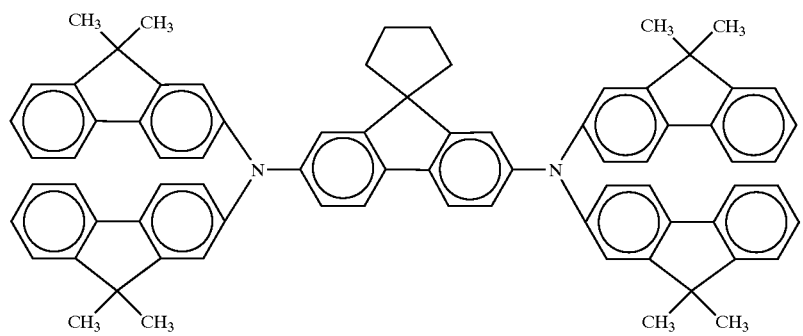
Compound 58
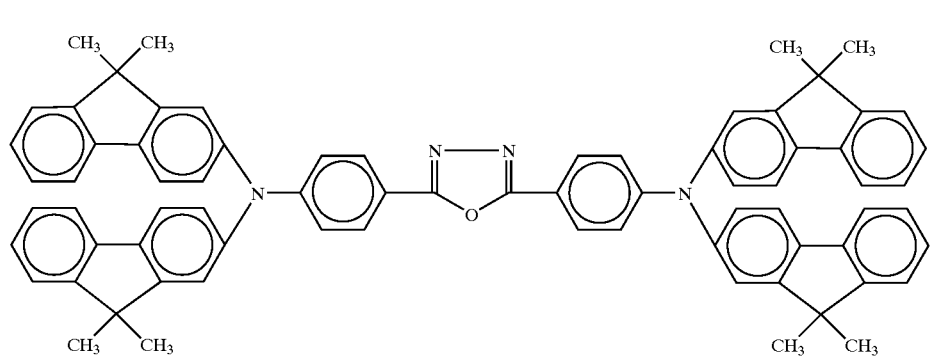
Compound 59

-continued
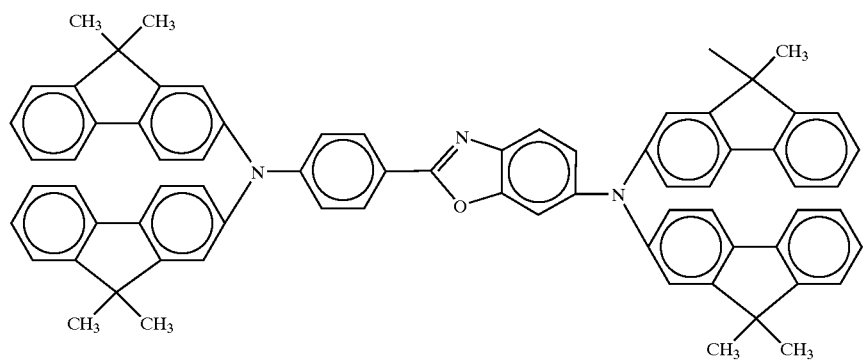
Compound 60
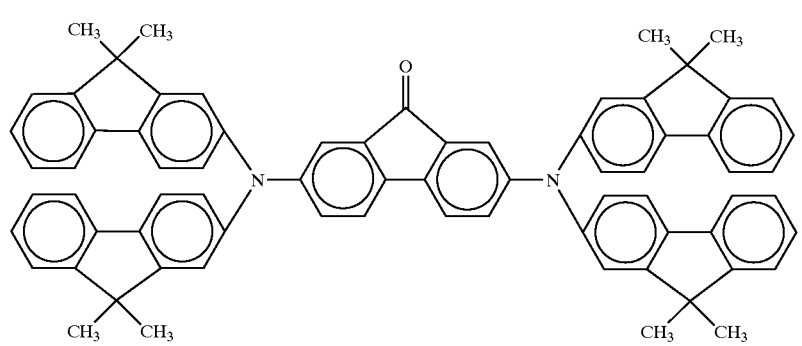
Compound 61
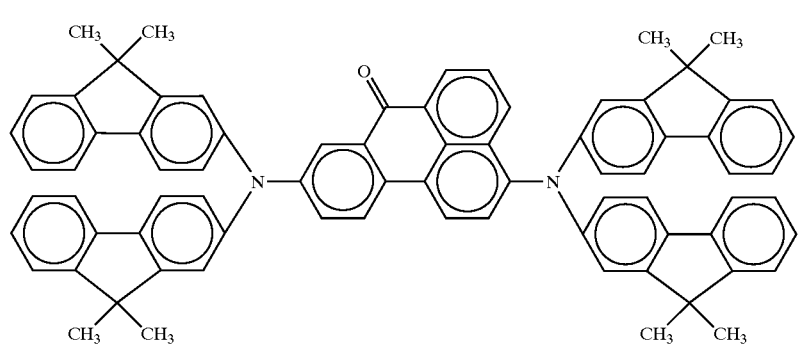
Compound 62
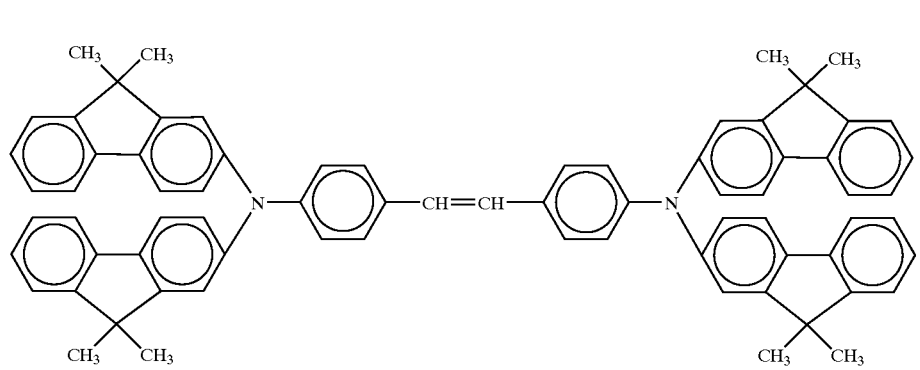
Compound 63

Compound 64
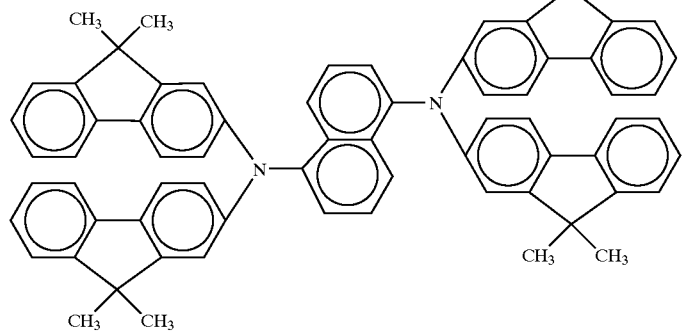
Compound 65
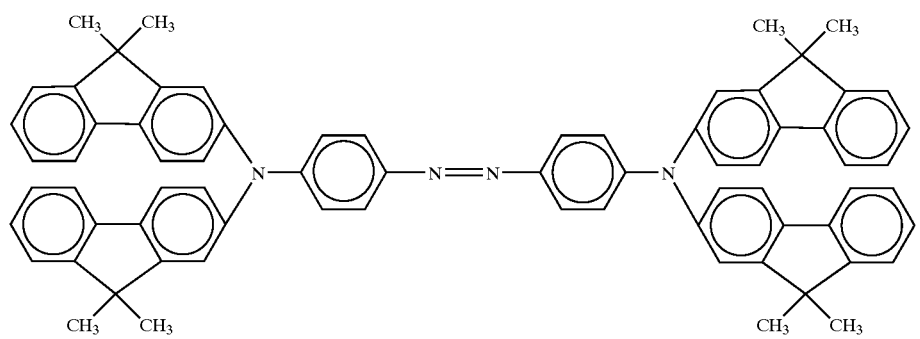
Compound 66
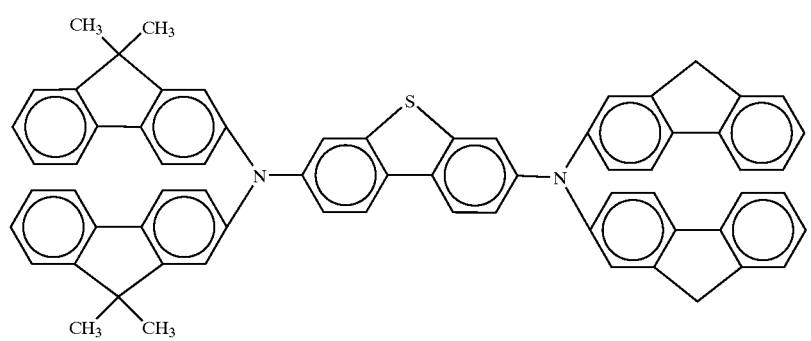
Compound 67
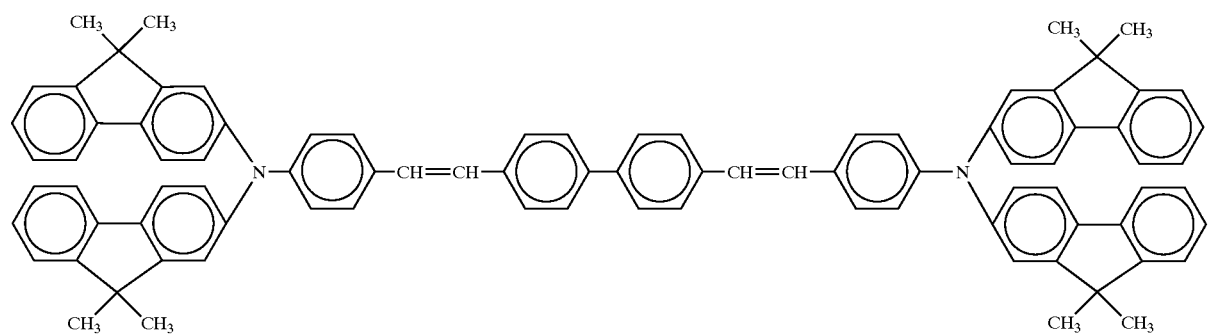

-continued
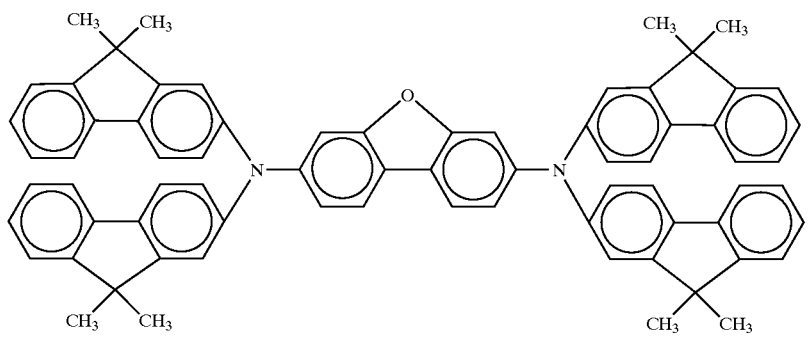
Compound 68
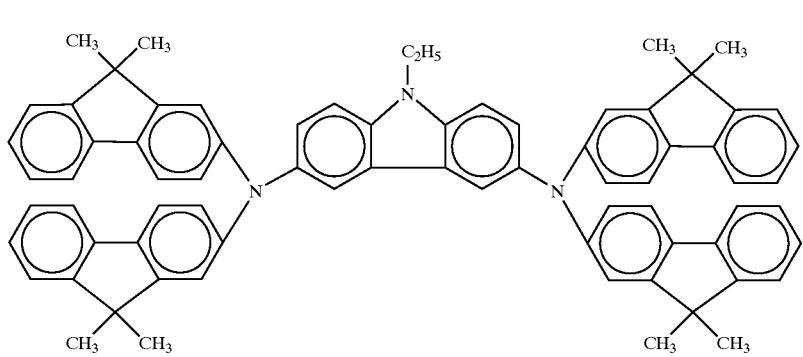
Compound 69
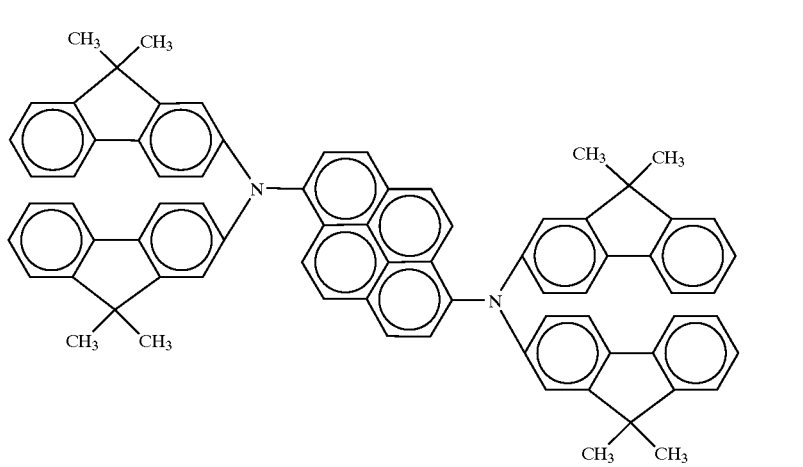
Compound 70
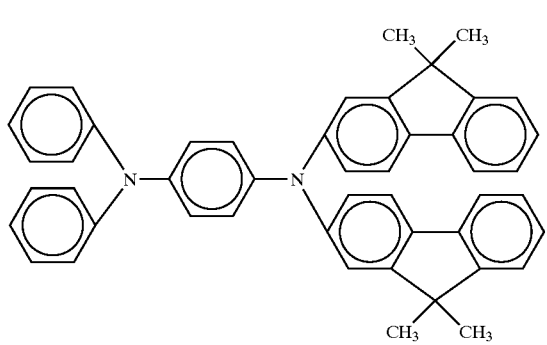
Compound 71

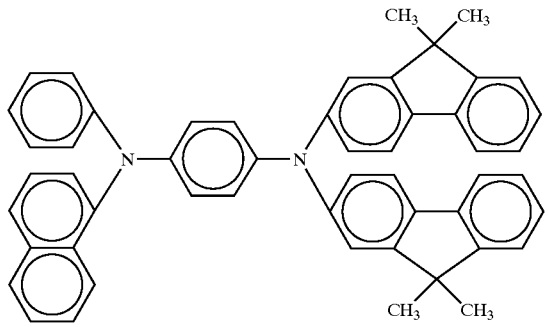
Compound 72
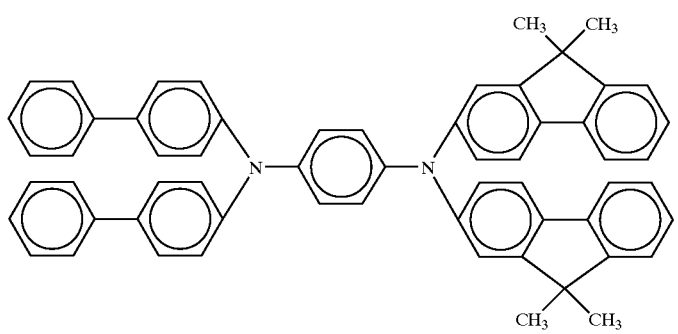
Compound 73
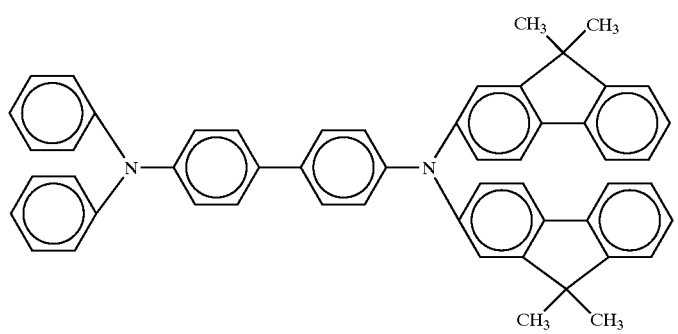
Compound 74
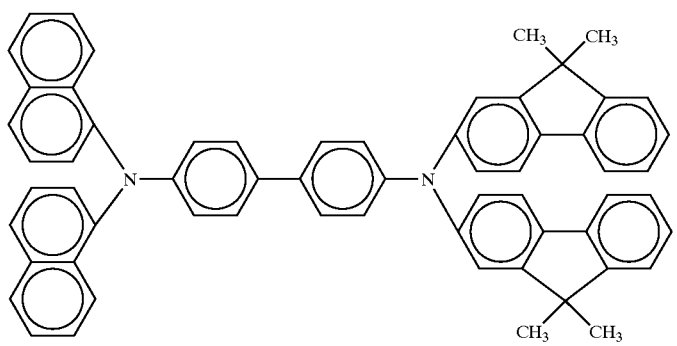
Compound 75

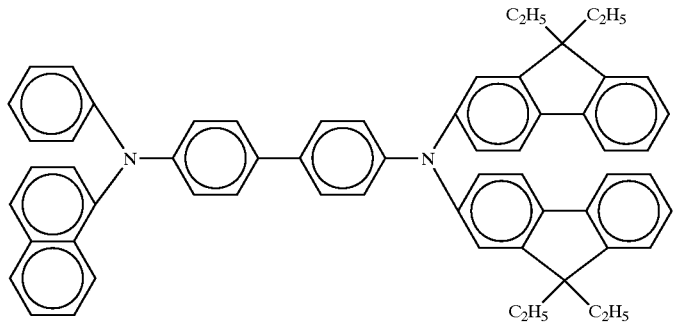
Compound 76
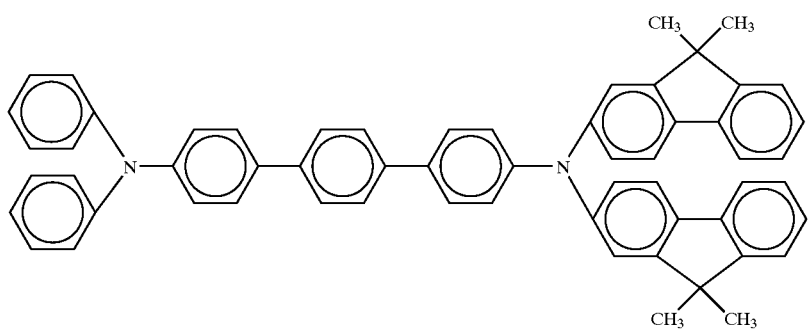
Compound 77
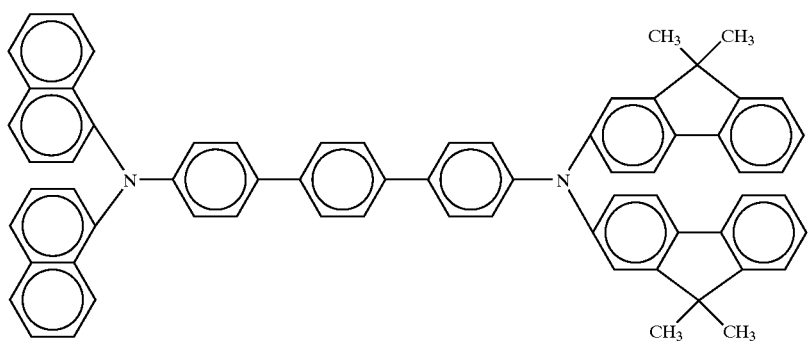
Compound 78
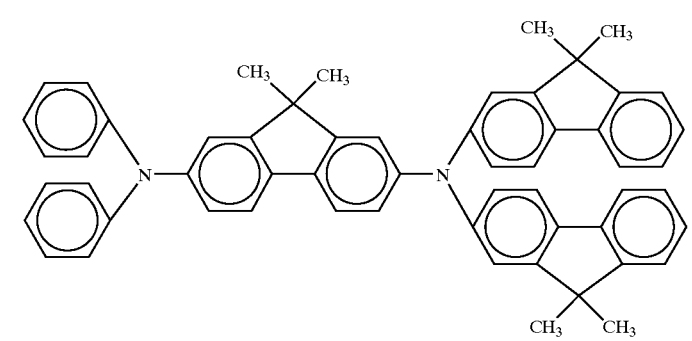
Compound 79

-continued
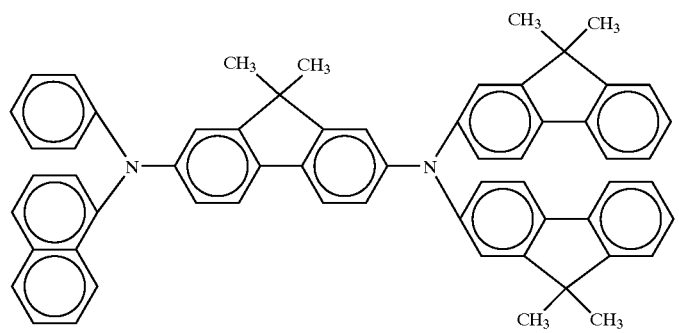
Compound 80
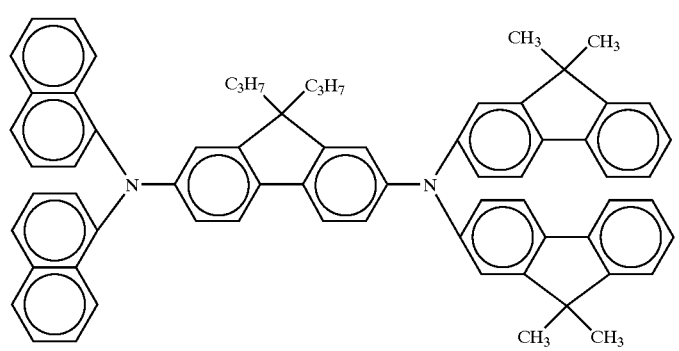
Compound 81
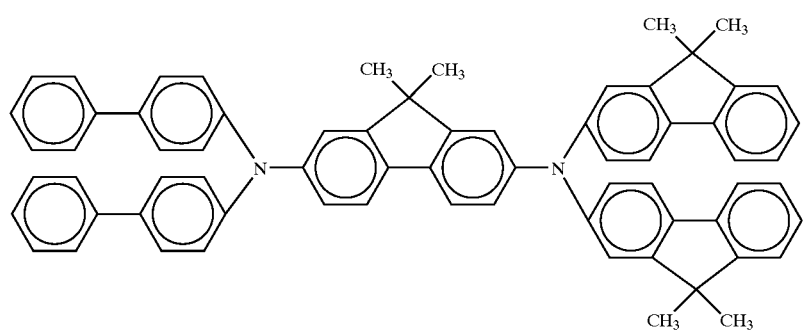
Compound 82
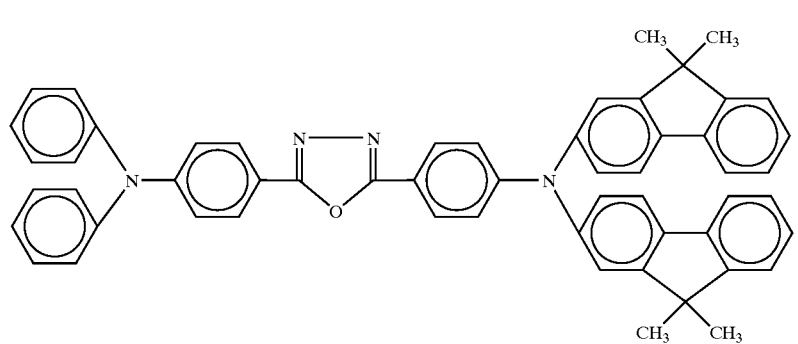
Compound 83

-continued
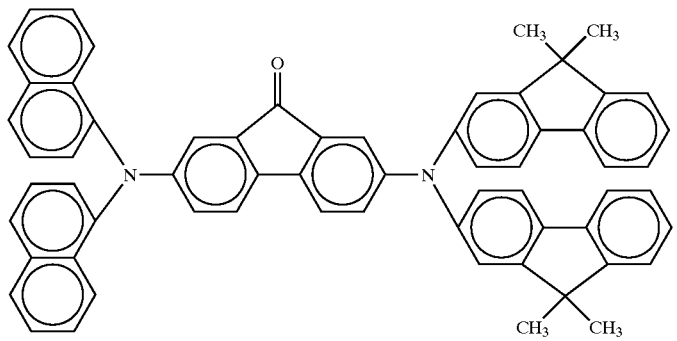
Compound 84
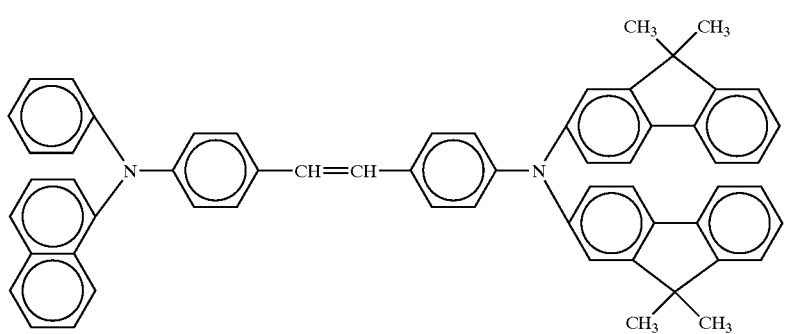
Compound 85
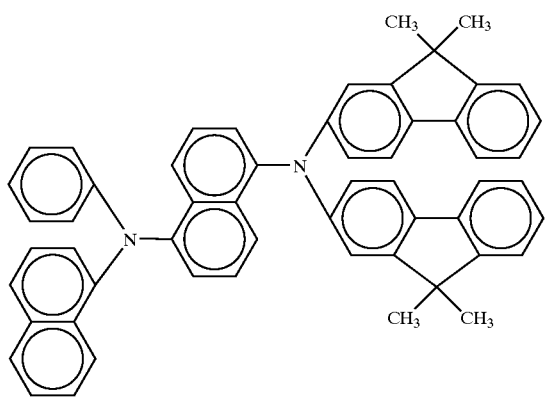
Compound 86
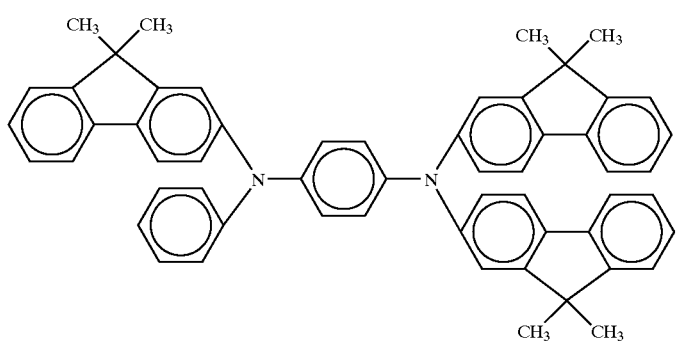
Compound 87

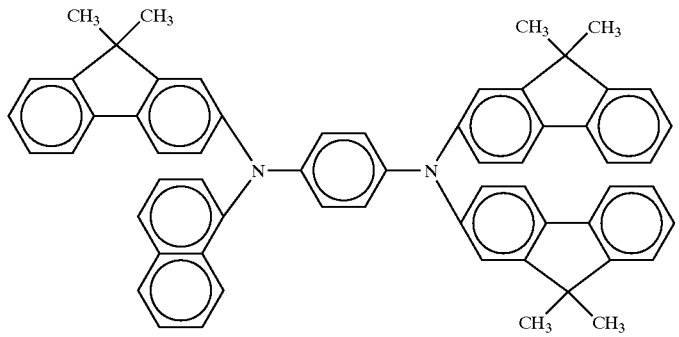
Compound 88
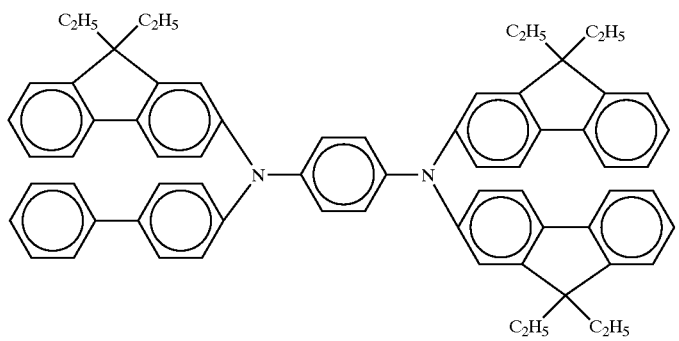
Compound 89
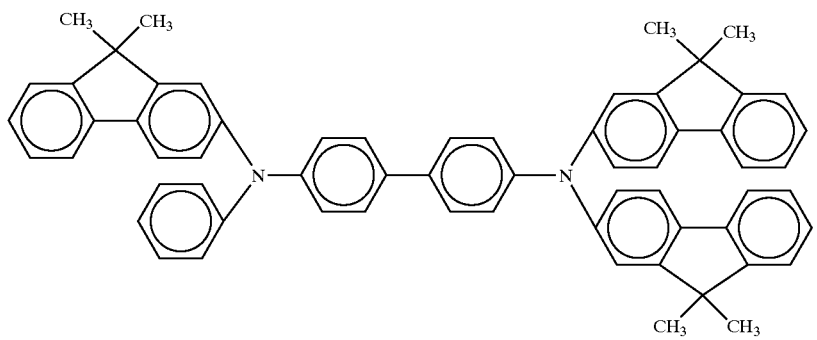
Compound 90
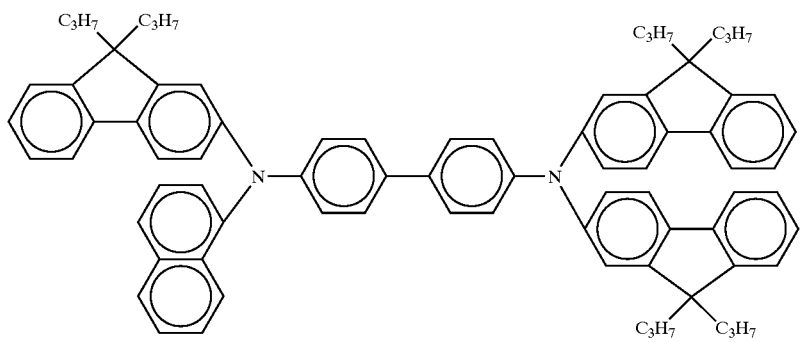
Compound 91

-continued
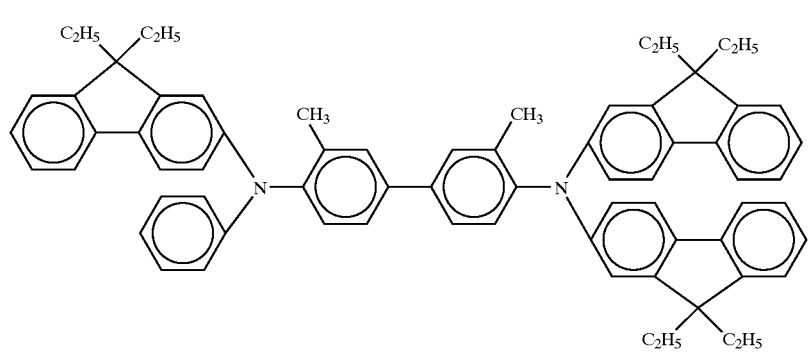
Compound 92
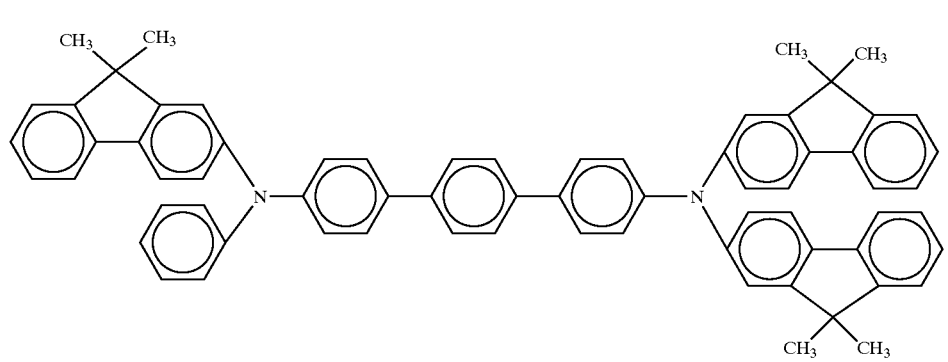
Compound 93
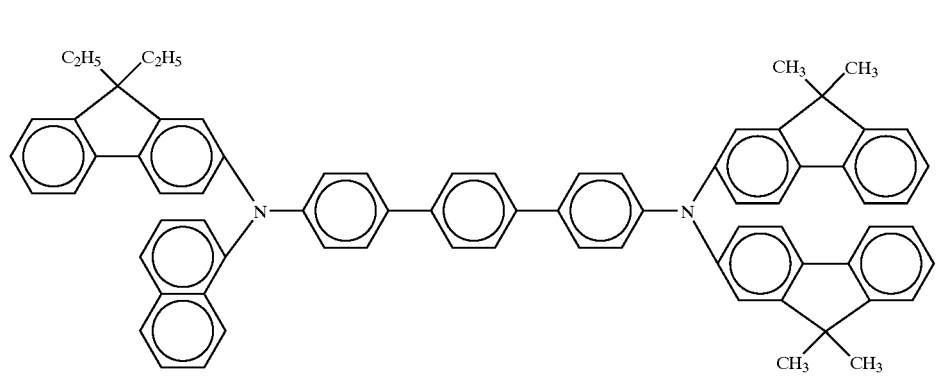
Compound 94
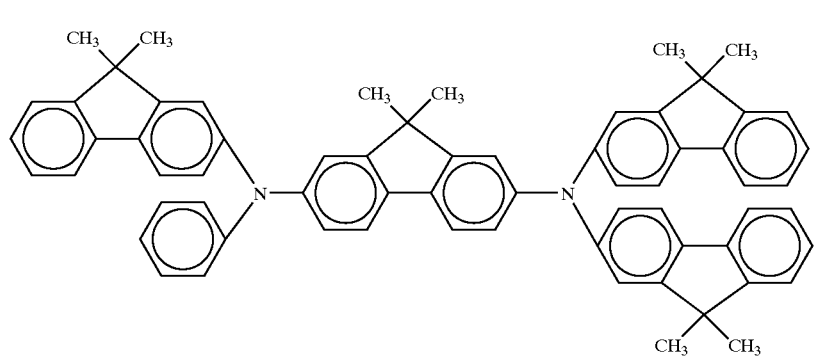
Compound 95

-continued
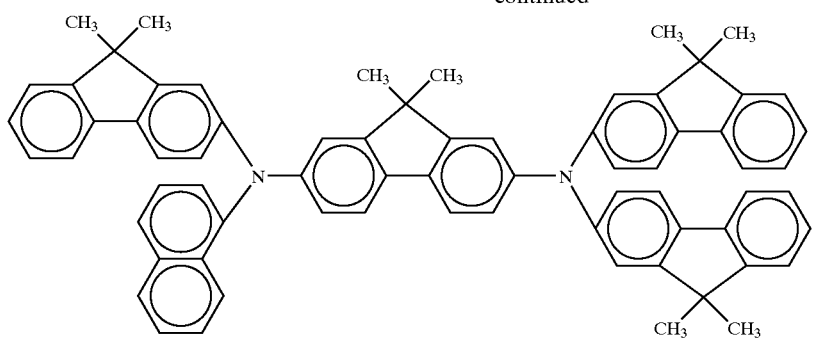
Compound 96
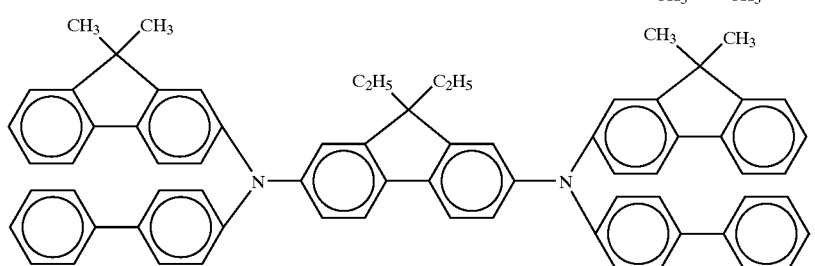
Compound 97
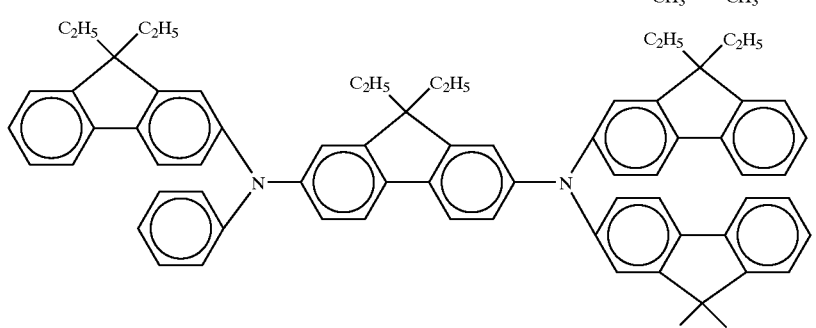
Compound 98
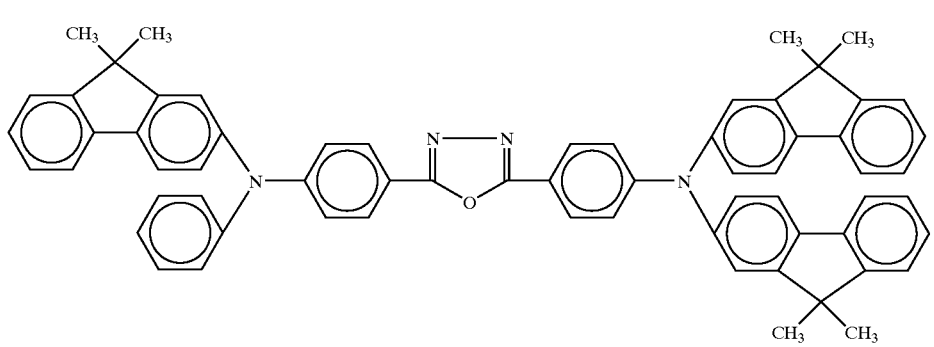
Compound 99
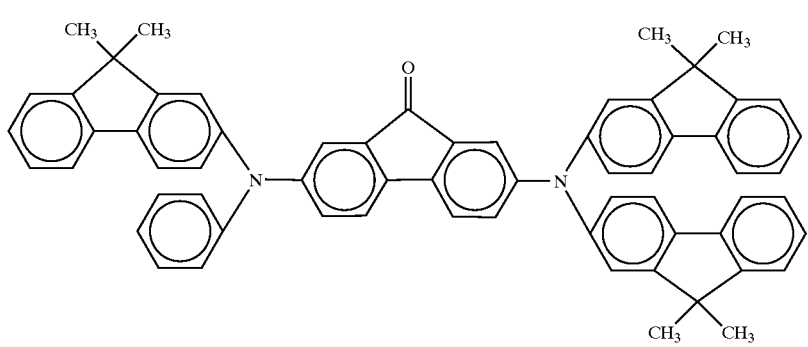
Compound 100

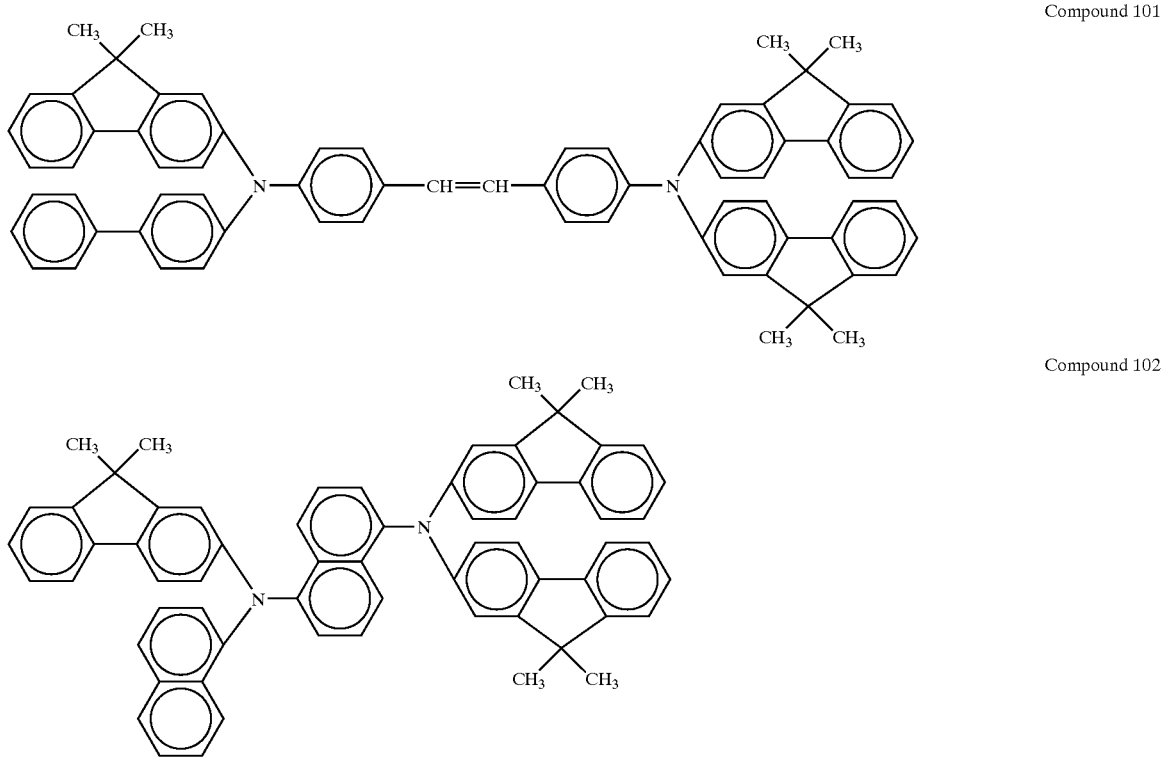

Compound 101

Compound 102

The present invention also includes an electroluminescent device. The electroluminescent device in accordance with the present invention comprises a pair of electrodes and an organic layer composed of the organic compound represented by the formula (1) displaced between the electrodes. The organic compound is formed between the positive and negative electrodes by a vacuum evaporation or solution coating process. The thickness of the organic layer is preferably 2 μm or less, more preferably 0.5 μm or less, and most preferably 1 nm to 500 nm.

In the electroluminescent device in accordance with the present invention, a plurality of layers may be provided between the two electrodes. In this case, at least one layer among these layers is composed of the compound represented by the formula (1). The luminescent color of the electroluminescent device can be determined by selecting the compound represented by the formula (1).

The electroluminescent device in accordance with the present invention will now be described in detail with reference to the drawings.

FIG. 1 is a schematic cross-sectional view of an embodiment of the electroluminescent device in accordance with the present invention. A positive electrode 2, a luminescent layer 3 and a negative electrode 4 are formed on a substrate 1 in that order. The luminescent layer 3 may be composed of a single compound having hole transportability, electron transportability and luminescence, or a mixture of compounds each having one of these properties.

Figure 2:
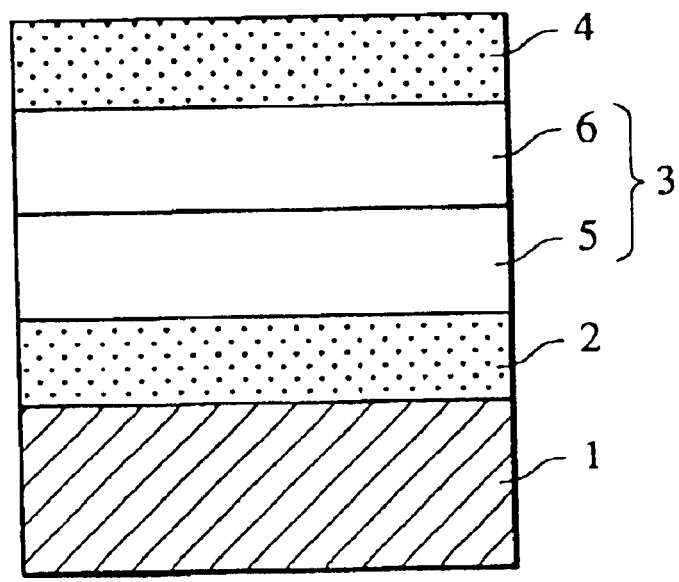
FIG. 2 is a schematic cross-sectional view of an embodiment of an electroluminescent device in accordance with the present invention.

FIG. 2 is a schematic cross-sectional view of another embodiment of the electroluminescent device in accordance with the present invention. A positive electrode 2, a hole transport layer 5, an electron transport layer 6 and a negative electrode 4 are formed on a substrate 1 in that order. The hole transport layer 5 and the electron transport layer 6 function as a luminescent layer 3. The hole transport layer 5 may be composed of a luminescent material having hole transportability or a mixture including such a material and a non-luminescent material having hole transportability. The luminescent and non-luminescent materials may also have electron transportability. The electron transport layer 6 may be composed of a luminescent material having electron transportability or a mixture including such a material and a non-luminescent material having electron transportability. The luminescent and non-luminescent materials may also have hole transportability.

Figure 3:
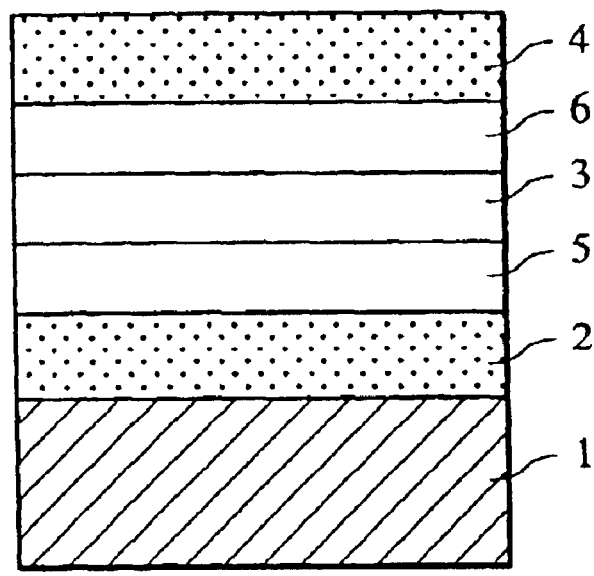
FIG. 3 is a schematic cross-sectional view of an embodiment of an electroluminescent device in accordance with the present invention.

FIG. 3 is a schematic cross-sectional view of a further embodiment of the electroluminescent device in accordance with the present invention. A positive electrode 2, a hole transport layer 5, a luminescent layer 3, an electron transport layer 6 and a negative electrode 4 are formed on a substrate 1 in that order. In this configuration, carrier transport and luminescence are performed in the individual layers. Such a configuration permits a wide variety of combinations of a material having excellent hole transportability, a material having excellent electron transportability and a material having excellent luminescence. Further, the configuration permits the use of various compounds emitting light with different wavelengths; hence the hue of the luminescent light can be controlled within a wide range. Trapping effectively holes and electrons (or excimers) in the central luminescent layer will increase the luminescent efficiency.

Figure 4:
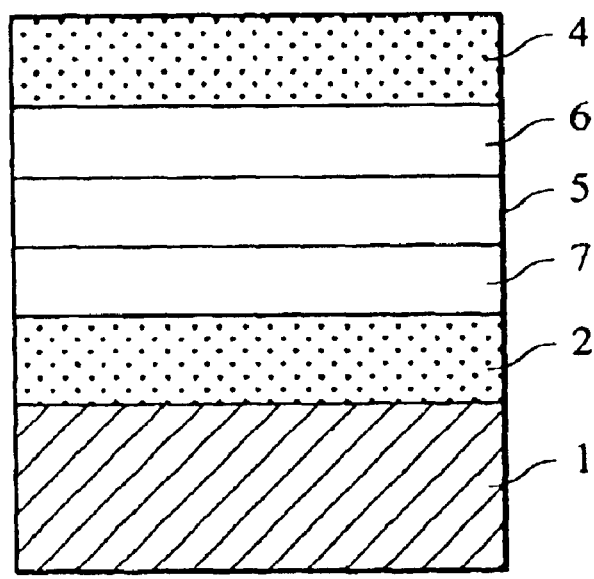
FIG. 4 is a schematic cross-sectional view of an embodiment of an electroluminescent device in accordance with the present invention.

FIG. 4 is a schematic cross-sectional view of a still further embodiment of the electroluminescent device in accordance with the present invention. A positive electrode 2, a hole injection/transport layer 7, a hole transport layer 5, an electron transport layer 6 and a negative electrode 4 are formed on a substrate 1 in that order.

The organic compound in accordance with the present invention represented by the formula (1) has excellent luminescence compared to known compounds, and can be used for the electroluminescent devices shown in FIGS. 1 to 4.

The organic compound represented by the formula (1) has hole transportability and/or carrier transportability depending on the types of the substituent groups. An organic compound or a combination of different organic compounds may be used in all the configurations shown in FIGS. 1 to 4. In the present invention, another layer or other layers composed of other materials other than the compound represented by the formula (1) can be provided in addition to at least one organic compound layer.

The organic compound represented by the formula (1) is used as a constituent in the luminescent layer or a charge transport layer. These layers may further include various compounds used in electrophotographic photosensitive members and the like. Examples of the compounds include hole transport materials, luminescent hole transport materials (for example, compounds shown in Tables 1 to 5), electron transport materials, and luminescent electron transport materials (for example, compounds shown in Tables 6 to 9).

Table 10 illustrates examples of dopant dyes. The addition of a trace amount of dopant dye in the luminescent layer will significantly increase the luminescent efficiency or will change the luminescent color.

TABLE 1

Hole Transfer Compounds

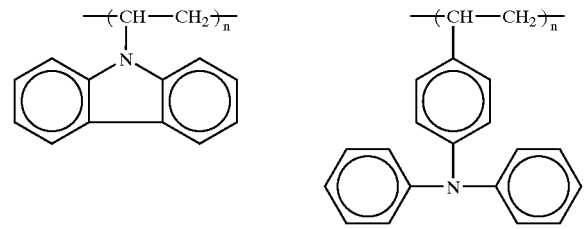

TABLE 1-continued

Hole Transfer Compounds

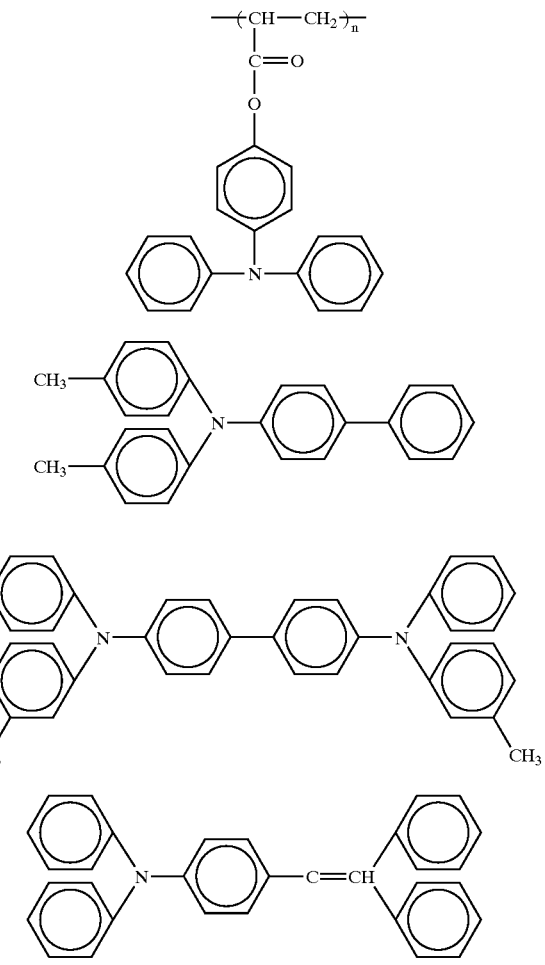

TABLE 2

Hole Transfer Compounds

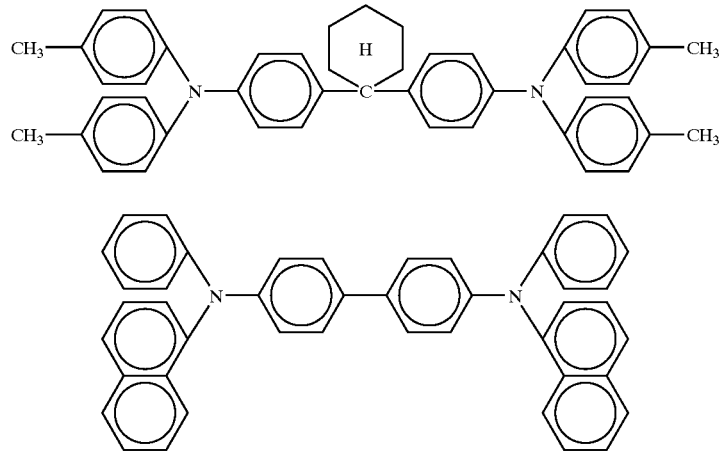

TABLE 2-continued
Hole Transfer Compounds
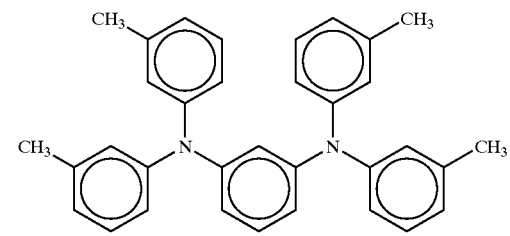
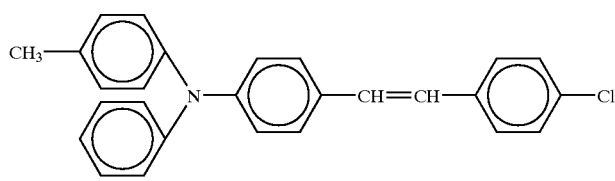
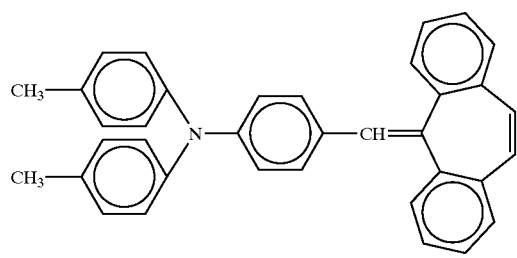
TABLE 3
Hole Transfer Compounds
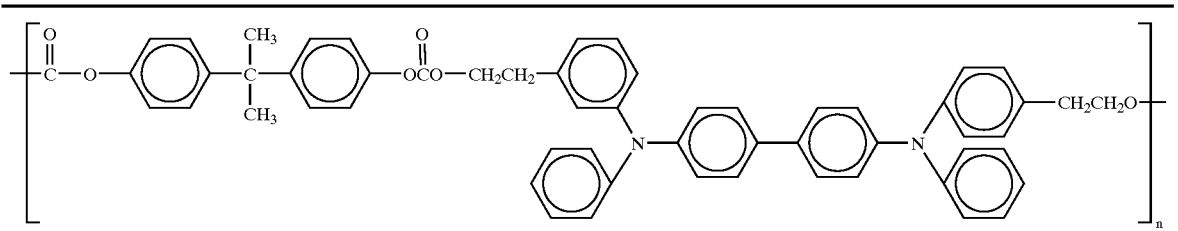
TABLE 4
Hole Transfer Compounds
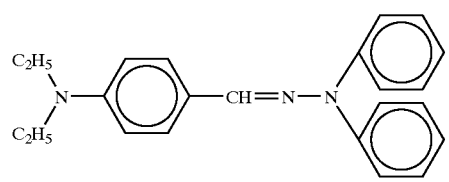
TABLE 4-continued
Hole Transfer Compounds
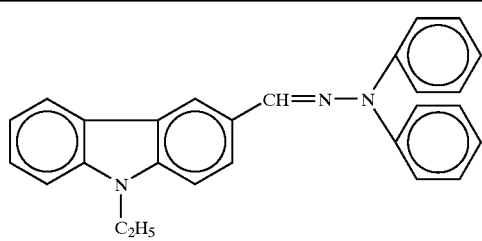

TABLE 4-continued
Hole Transfer Compounds
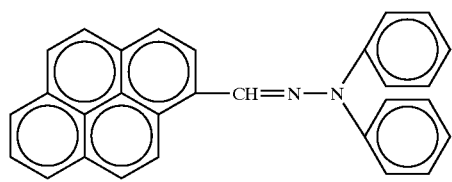
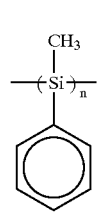 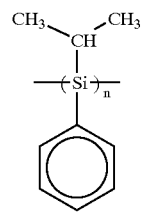
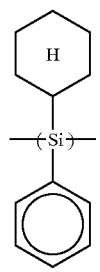 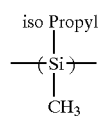
TABLE 5
Hole Transfer Compounds
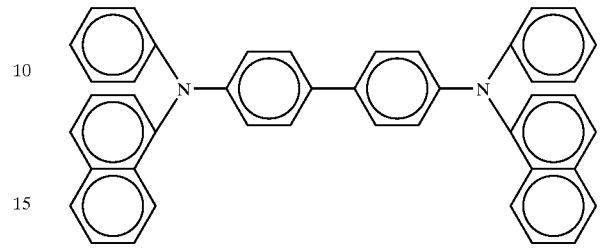
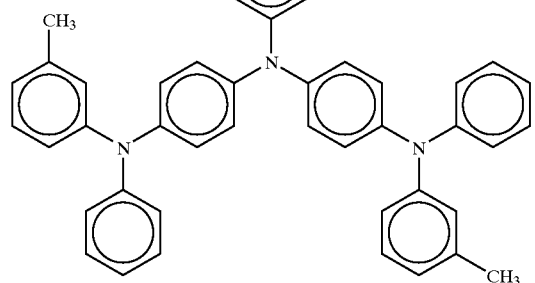
TABLE 6
Electron Transport Compounds
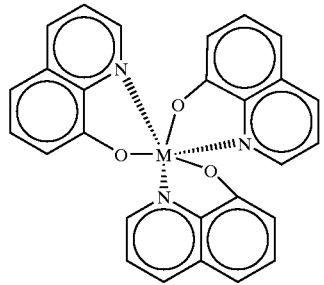 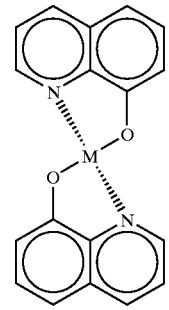
M: Al, Ga        M: Zn, Mg, Be

TABLE 6-continued
Electron Transport Compounds
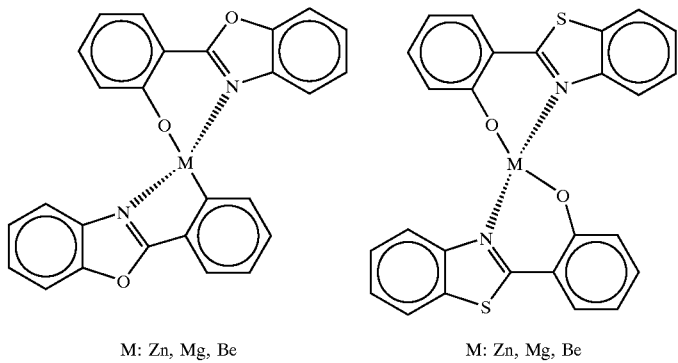
M: Zn, Mg, Be        M: Zn, Mg, Be
TABLE 7
Electron Transport Compounds
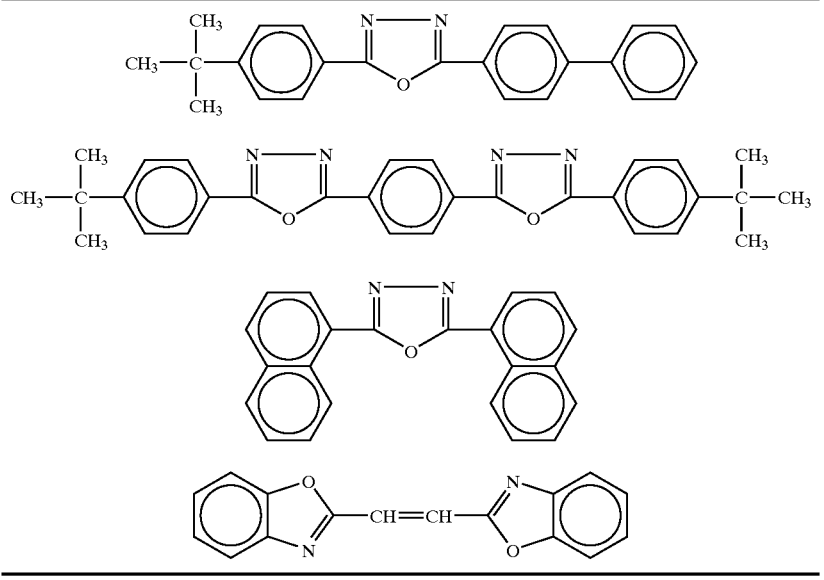
TABLE 8
Electron Transport Compounds
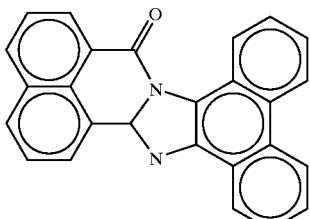
TABLE 8-continued
Electron Transport Compounds
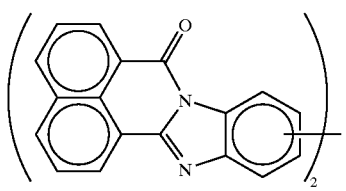
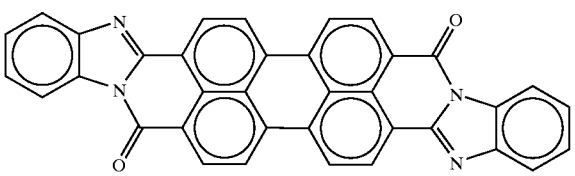

TABLE 8-continued

Electron Transport Compounds

TABLE 9

Electron Transport Compounds

TABLE 10

Dopant Dyes

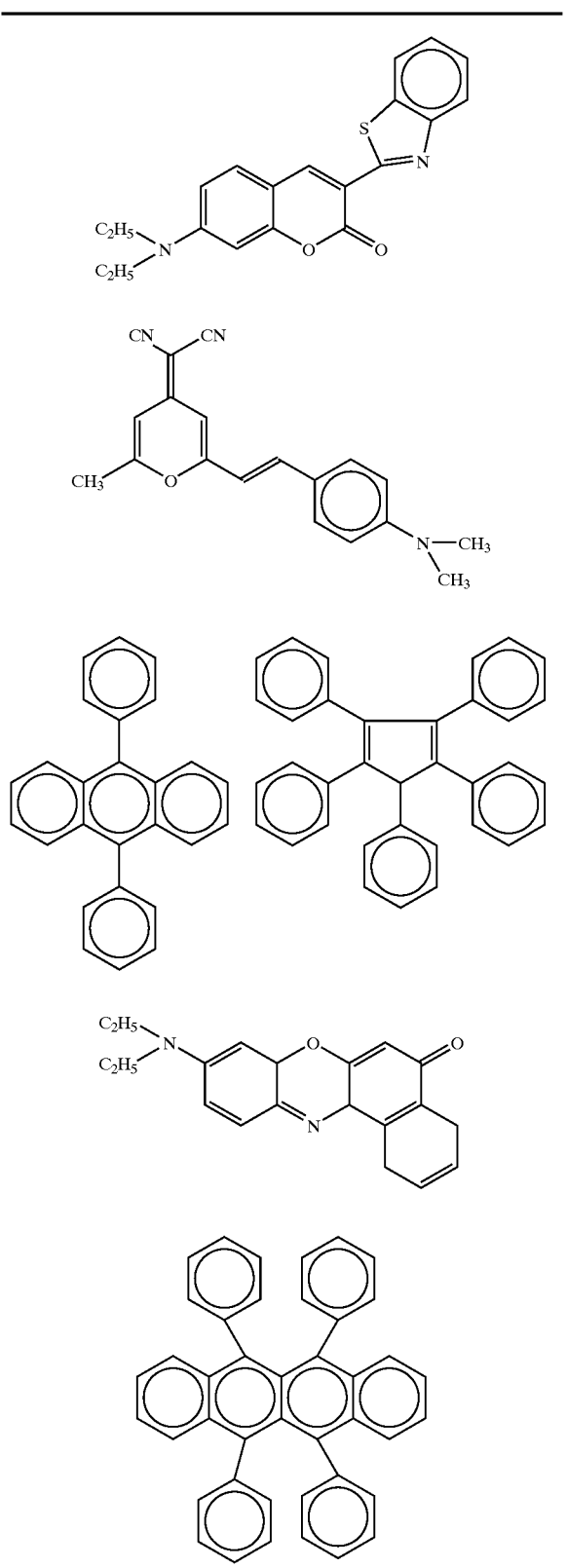

TABLE 10-continued

Dopant Dyes

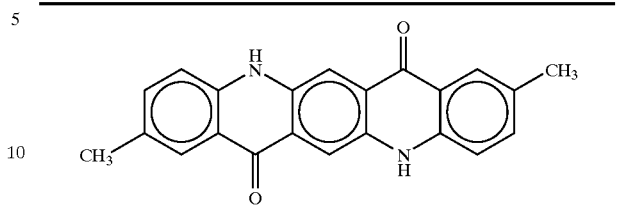

In the electroluminescent device in accordance with the present invention, each layer on the substrate is formed by a vacuum evaporation process or a coating process using a combination of the relevant compound and a suitable binding resin.

Non-limiting examples of the binding resins include polyvinyl carbazole resins, polycarbonate resins, polyester resins, polyarylate resins, butyral resins, polystyrene resins, polyvinyl acetal resins, diallyl phthalate resins, acrylate resins, methacrylate resins, phenol resins, epoxy resins, silicon resins, polysulfone resins, and urea resins. These binding resins can be used alone or in combination.

Materials for the positive electrode have preferably large work functions. Examples of preferred materials include nickel, gold, platinum, palladium, selenium, rhenium, and iridium, alloys thereof, tin oxide, indium tin oxide (ITO), and copper iodide. Also, conductive polymers, such as poly(3-methylthiophene), polyphenylene sulfide and polypyrrole, can be used.

Preferred materials for the negative electrode have small work functions. Examples of such materials include silver, lead, tin, magnesium, aluminum, calcium, manganese, indium and chromium, and alloys thereof.

It is preferable that at least one of the materials for the positive and negative electrodes has a transmittance of at least 50% at the wavelength range of the light emerging from the electroluminescent device.

Examples of transparent substrates used in the present invention include glass plates and plastic films.

EXAMPLES

To further illustrate the present invention, and not by way of limitation, the following examples are given.

Example 1

Synthesis of N,N,N',N'-tetra[2-(9,9-dimethylfluorenyl)]-2,7-diamino-9,9-dimethylfluorene (Compound 48)

Into a 100-ml egg-plant-type flask with a reflux condenser, 2.24 g of 2,7-diamino-9,9-dimethylfluorene, 19.21 g of 2-iodo-9,9-dimethylfluorene, 7.5 g of platinum carbonate, 6.0 g of copper powder and 50 ml of o-dichlorobenzene were fed, and refluxed with stirring for 32 hours. The solution was cooled and filtrated. The dichlorobenzene solution was concentrated by evaporation, and then toluene was added to precipitate crude crystals. The crude product was dissolved into a toluene/hexane mixture, and purification was accomplished by passing the solution through a silica gel column. A pale yellow fine crystal of N,N,N',N'-tetra[2-(9,9-dimethylfluorenyl)]-2,7-diamino-9,9-dimethylfluorene (5.41 g; yield: 54.6%) represented by the following formula was obtained.

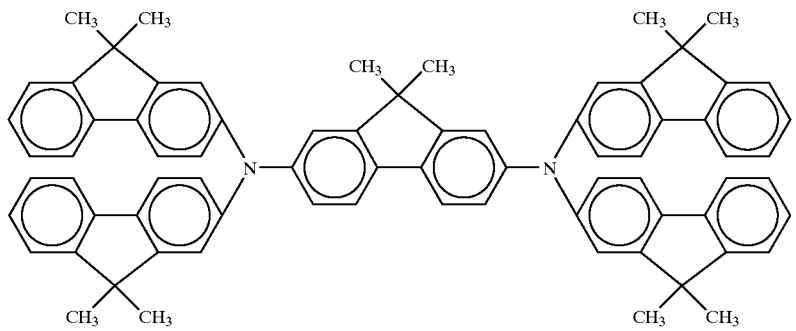

Figure 5:
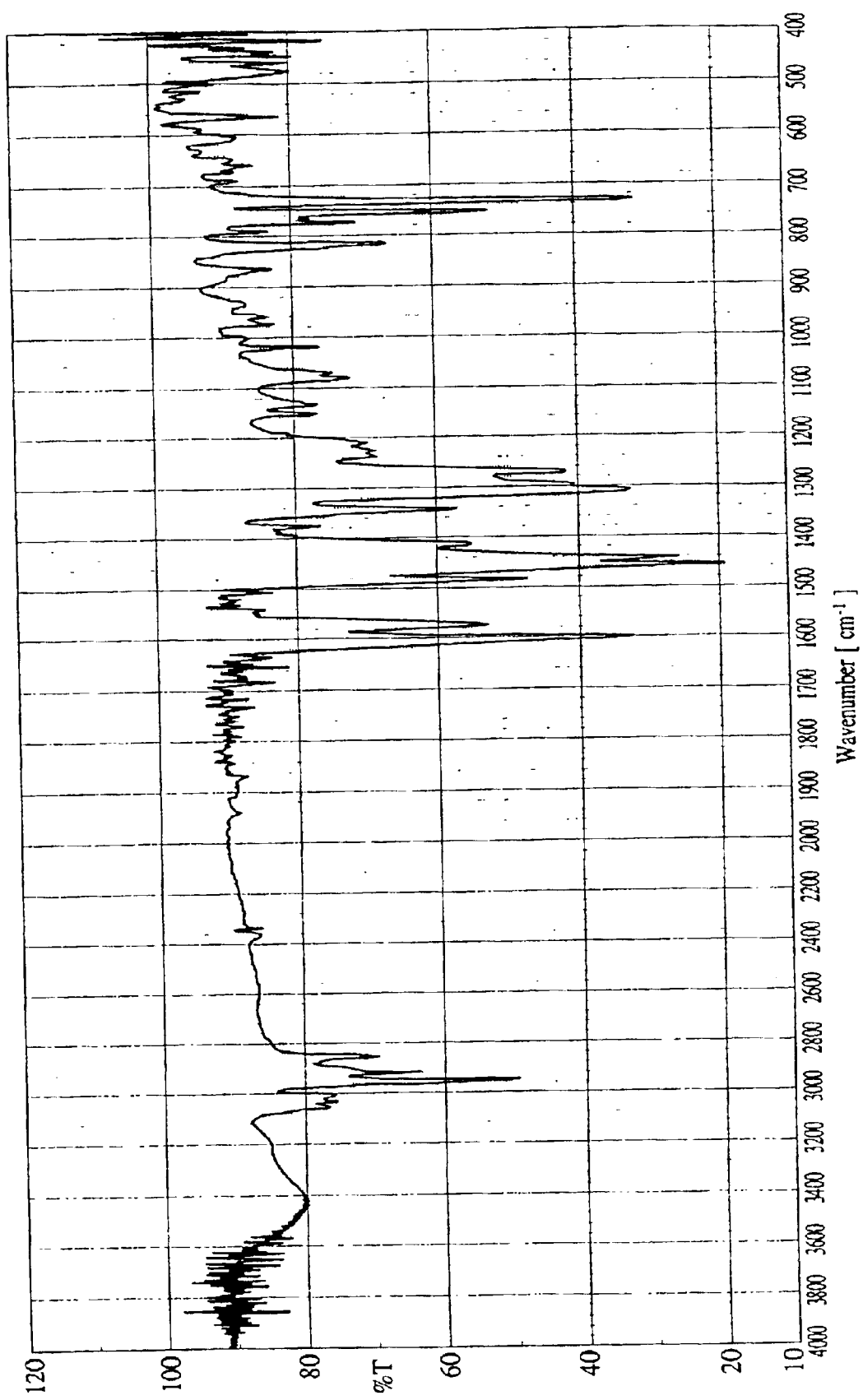
FIG. 5 is an IR spectrum of Compound 48 synthesized in Example 1 in accordance with the present invention.

The product had a melting point (Tm) of ranging from 309.0° C. to 310.5° C. and a glass transition temperature (Tg) of 186° C. which were determined by a differential scanning calorimeter made by Perkin-Elmer Corporation. An infrared spectrum of the product was taken with a JASCO FT-IR spectrometer. The spectrum is shown in FIG. 5.

Example 2

Synthesis of N,N'-di(4-biphenyl)-N,N'-di[2-(9,9-dimethylfluorenyl)]-4,4'-diaminobiphenyl (Compound 7)

Into a 100-ml egg-plant-type flask with a reflux condenser, 4.88 g of N,N'-diphenylbenzidine, 6.40 g of 2-iodo-9,9-dimethylfluorene, 4.00 g of platinum carbonate, 3.0 g of copper powder and 30 ml of o-dichlorobenzene were fed, and refluxed with stirring for 20 hours. The solution was cooled and filtrated. The dichlorobenzene solution was concentrated by evacuation, and then methanol was added to precipitate crude crystals. The crude product was dissolved into a toluene/hexane mixture, and purification was accomplished by passing the solution through a silica gel column. A pale yellow fine crystal of N,N'-di(4-biphenyl)-N,N'-di[2-(9,9-dimethylfluorenyl)]-4,4'-diaminobiphenyl (5.50 g; yield: 63.0%) represented by the following formula was obtained.

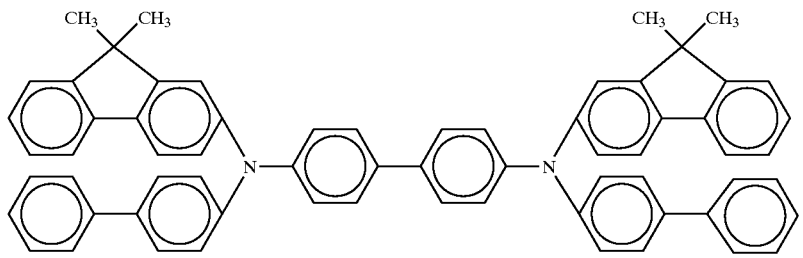

Figure 6:
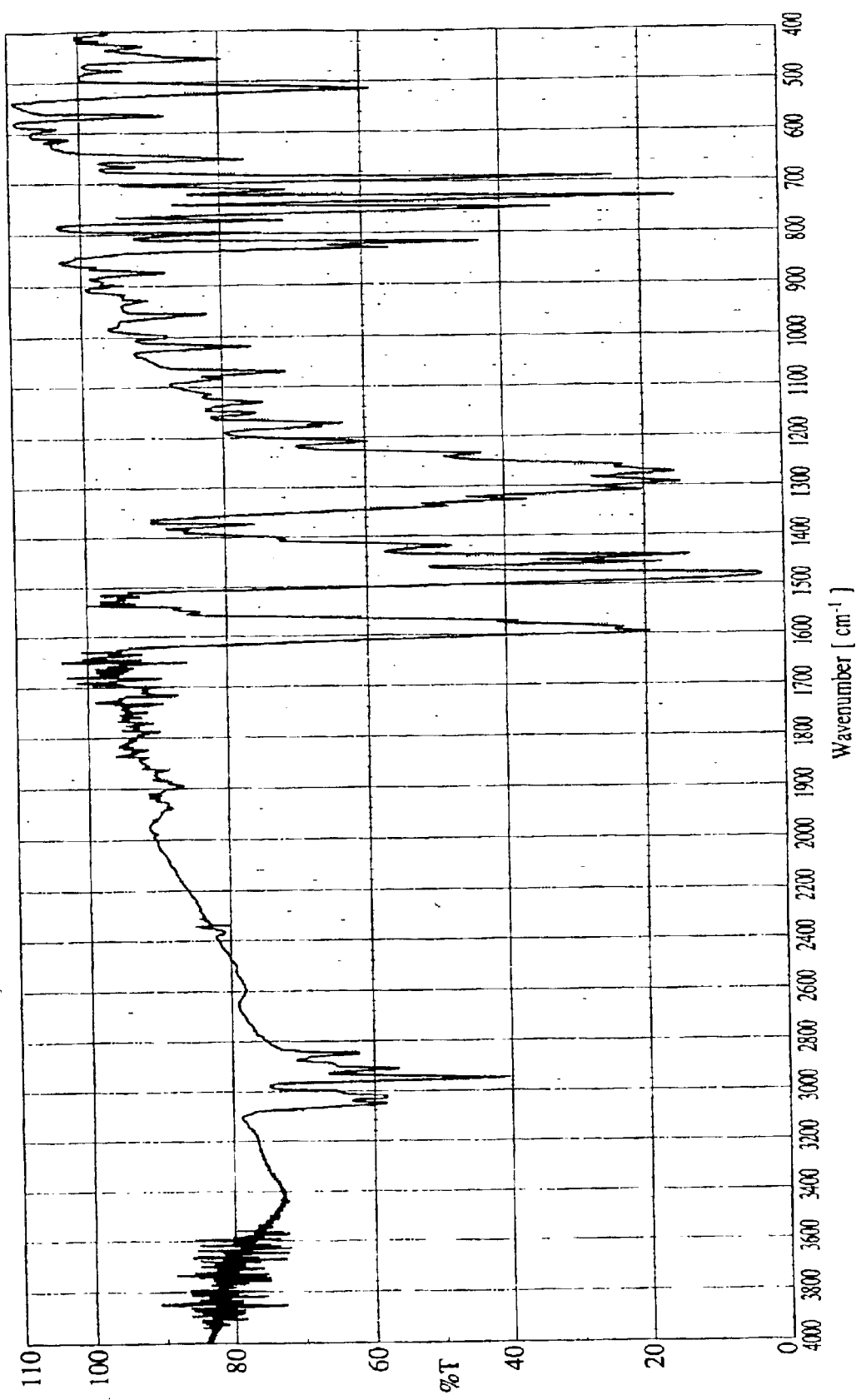
FIG. 6 is an IR spectrum of Compound 7 synthesized in Example 7 in accordance with the present invention.

The product had a melting point (Tm) ranging from 267.0° C. to 268.5° C. and a glass transition temperature (Tg) of 120.5° C. which were determined as in Example 1. An infrared spectrum taken as in Example 1 is shown in FIG. 6.

Example 3

An electroluminescent device was prepared to determine the luminance.

An indium tin oxide (ITO) layer with a thickness of 100 nm was formed on a glass substrate, and the transparent substrate was washed. An organic layer with a thickness of 65 nm composed of Compound 13 was formed on the transparent substrate, and an aluminum quinolinol layer with a thickness of 65 nm was formed thereon. A metallic electrode having a composition of Mg:Ag=10:1 by atomic ratio was deposited thereon by a vacuum deposition process to form an organic EL device, wherein the vacuum degree was 3 to $4\times10^{-6}$ torr, and the deposition rates of the organic layer and the metallic electrode were 0.2 to 0.3 nm/sec and 2.0 nm/sec, respectively.

A direct current of 11 V was applied between the ITO positive electrode and the Mg/Ag negative electrode of the device. A current flow of 37 mA/cm$^2$ and a green luminescence having a luminance of 2,130 cd/m$^2$ were observed. A voltage with a current density of 4.7 mA/cm$^2$ was applied to the device for 100 hours in a nitrogen stream. The luminance was 180 cd/m$^2$ at the start and slightly changed to 155 cd/m$^2$ at the end.

Examples 4 to 8

Electroluminescent devices were prepared and evaluated as in Example 3 using Compound 8, 38, 48, 51 and 52 instead of the Compound 13.

The results are shown in Table 11.

TABLE 11

| | | Initial | | After 100 hours | |
|---|---|---|---|---|---|
| Example | Compound | Applied voltage (V) | Luminance (cd/m$^2$) | Applied voltage (V) | Luminance (cd/m$^2$) |
| 4 | 8 | 7.5 | 180 | 7.9 | 160 |
| 5 | 38 | 9.1 | 200 | 10.4 | 175 |

TABLE 11-continued

| | | Initial | | After 100 hours | |
|---|---|---|---|---|---|
| Example | Compound | Applied voltage (V) | Luminance (cd/m$^2$) | Applied voltage (V) | Luminance (cd/m$^2$) |
| 6 | 48 | 6.3 | 210 | 7.3 | 200 |
| 7 | 51 | 6.2 | 215 | 7.0 | 210 |
| 8 | 52 | 8.4 | 190 | 9.5 | 140 |

Comparative Example 1

An electroluminescent device was prepared and evaluated as in Example 3 using the following compound instead of the Compound 13.

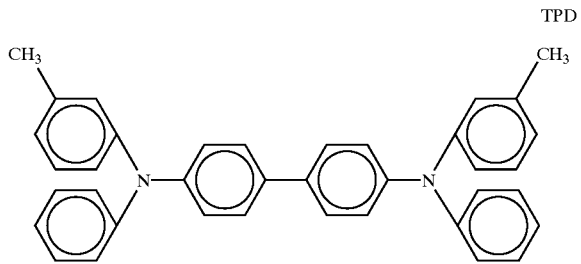

TPD

A direct current of 15 V was applied between the ITO positive electrode and the Mg/Ag negative electrode. A current flow of 15 mA/cm$^2$ and a green luminescence having a luminance of 35 cd/m$^2$ were observed. A voltage with a current density of 27 mA/cm$^2$ was applied to the device for 100 hours in a nitrogen stream. The luminance was 100 cd/m$^2$ at the start and significantly decreased to 8 cd/m$^2$ at the end.

The results of Examples 3 to 8 and Comparative Example 1 demonstrate that the electroluminescent devices using the organic compounds in accordance with the present invention have high luminance and prolonged life.

Example 9

An electroluminescent device having a configuration as shown in FIG. 4 was produced. A transparent glass substrate 1 provided with an ITO positive electrode 2 having a thickness of 100 nm deposited by a sputtering process was washed. Next, a hole injection/transfer layer 7 with a thickness of 20 nm was formed using Compound 53 on the transparent substrate, and then a hole transport layer 5 of 50 nm was formed thereon using a hole transport compound TPD represented by the following formula.

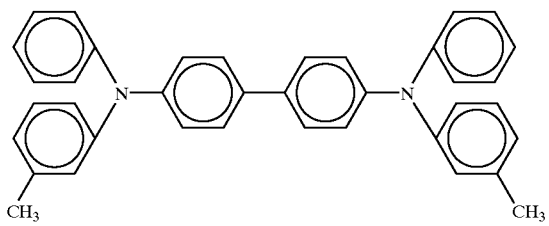

TPD

An electron transport layer 6 of 65 nm was formed thereon using an electron transport compound (Alq$_3$) represented by the following formula, and then an aluminum negative electrode 4 of 150 nm was formed.

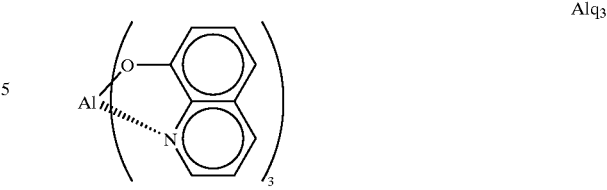

Alq$_3$

A direct current of 15 V was applied between the ITO positive electrode and the Al negative electrode. A current flow of 230 mA/cm$^2$ and a green luminescence having a luminance of 23,000 cd/m$^2$ were observed. A voltage with a current density of 4.3 mA/cm$^2$ was applied to the sample for 100 hours in a nitrogen stream. The luminance was 200 cd/m$^2$ at the start and slightly decreased to 185 cd/m$^2$ at the end.

Example 10

A transparent glass substrate provided with an ITO layer having a thickness of 100 nm deposited by a sputtering process was washed. Next, a hole transfer layer 5 with a thickness of 60 nm was formed using Compound 46 on the transparent substrate, and then a luminescent layer 3 of 10 nm was formed thereon using a fluorescent dye DCM represented by the following formula.

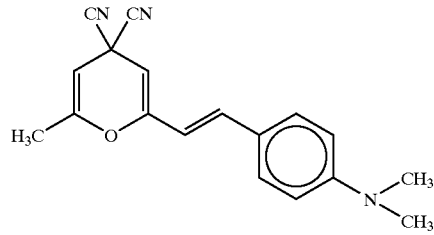

DCM

An electron transport layer 6 of 65 nm was formed thereon using the above-mentioned-electron transport compound (Alq$_3$), and then an aluminum negative electrode 4 of 150 nm was formed. An electroluminescent device having a configuration as shown in FIG. 3 was thereby formed.

A direct current of 17 V was applied between the ITO positive electrode and the Al negative electrode. A current flow of 150 mA/cm$^2$ and an orange luminescence having a luminance of 3,170 cd/m$^2$ were observed. A voltage with a current density of 5.1 mA/cm$^2$ was applied to the sample for 100 hours in a nitrogen stream. The luminance was 100 cd/m$^2$ at the start and slightly decreased to 85 cd/m$^2$ at the end.

Example 11

A transparent glass substrate provided with an ITO layer having a thickness of 100 nm deposited by a sputtering process was washed. Next, 0.10 g of Compound 17 and 0.01 g of an oxadiazole compound (OXD-7) represented by the formula below, and a polycarbonate resin having a weight average molecular weight of 35,000 were dissolved into 25 ml of tetrahydrofuran to prepare a coating solution. The coating solution was applied onto the transparent substrate by a dip coating process to form a coating layer with a thickness of 120 nm as a luminescent layer. A Mg/In metallic electrode with a thickness of 150 nm was deposited thereon to form a device having the configuration shown in FIG. 1.

A direct current of 12 V was applied between the ITO positive electrode and the Mg/In negative electrode. A current flow of 25 mA/cm$^2$ and a bluish green luminescence having a luminance of 250 cd/m$^2$ were observed. A voltage with a current density of 10 mA/cm$^2$ was applied to the sample for 100 hours. The luminance was 130 cd/m$^2$ at the start and slightly decreased to 95 cd/m$^2$ at the end.

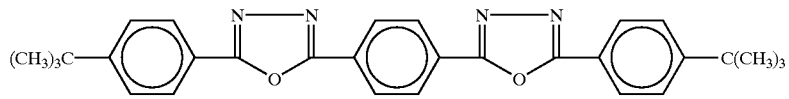

OXD-7

Comparative Example 2

An electroluminescent device was prepared as in Example 3 using a compound represented by the following formula instead of the Compound 13.

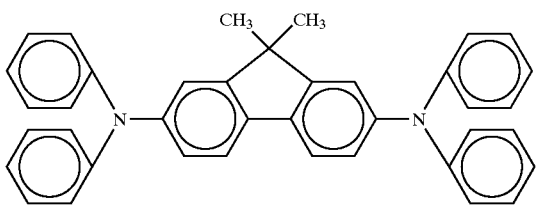

A direct current of 15 V was applied between the ITO positive electrode and the Mg/Ag negative electrode. A current flow of 20 mA/cm$^2$ and a green luminescence having a luminance of 41 cd/m$^2$ were observed. A voltage with a current density of 15 mA/cm$^2$ was applied to the sample for 100 hours. The luminance was 30 cd/m$^2$ at the start and changed to less than 1 cd/m$^2$ at the end.

While the present invention has been described with reference to what are presently considered preferred embodiments, the invention is not limited to the disclosed embodiments. To the contrary, the invention is intended to cover various modifications and equivalent arrangements, included within the spirit and scope of the appended claims. The scope of the following claims is to be accorded the broadest interpretation so as to encompass all such modifications and equivalent structures and functions.

What is claimed is:

1. An organic compound represented by the following formula:

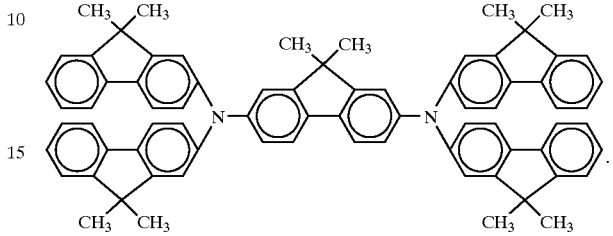

2. An electroluminescent device comprising a pair of electrodes and an organic compound according to claim 1 interposed between said electrodes.

3. An organic compound represented by the following formula:

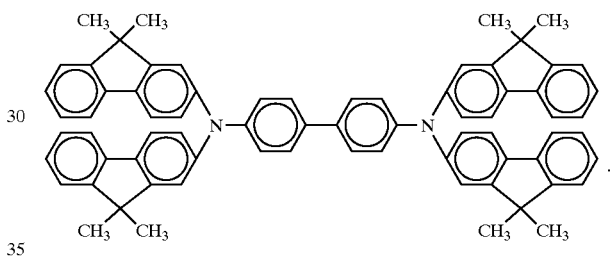

4. An electroluminescent device comprising a pair of electrodes and an organic compound according to claim 3 interposed between said electrodes.

* * * * *

UNITED STATES PATENT AND TRADEMARK OFFICE
CERTIFICATE OF CORRECTION

PATENT NO. : 6,858,325 B2  Page 1 of 2
DATED : February 22, 2005
INVENTOR(S) : Akihiro Senoo et al.

It is certified that error appears in the above-identified patent and that said Letters Patent is hereby corrected as shown below:

Title page,
Item [56], References Cited, OTHER PUBLICATIONS, after "W. Helfrich et al." reference, (second occurrence), "n" should read -- in --.

Column 11,
Lines 15-26,

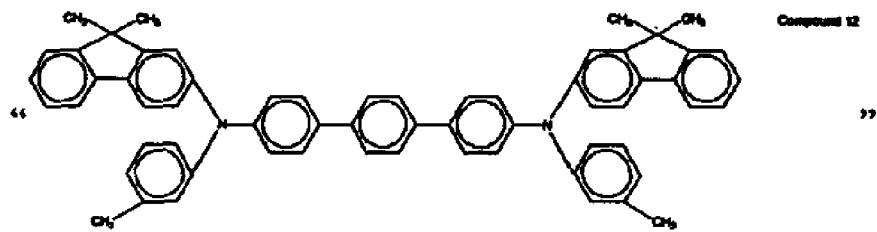

should read

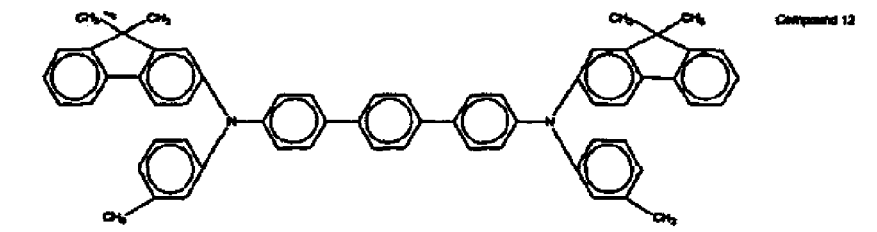

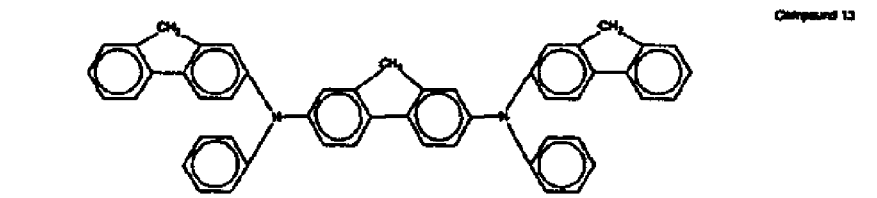

UNITED STATES PATENT AND TRADEMARK OFFICE
CERTIFICATE OF CORRECTION

PATENT NO. : 6,858,325 B2
DATED : February 22, 2005
INVENTOR(S) : Akihiro Senoo et al.

Page 2 of 2

It is certified that error appears in the above-identified patent and that said Letters Patent is hereby corrected as shown below:

Column 41,
Lines 35-50,

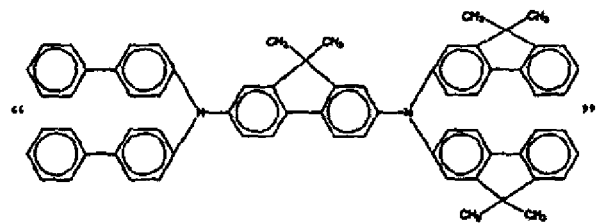

should read

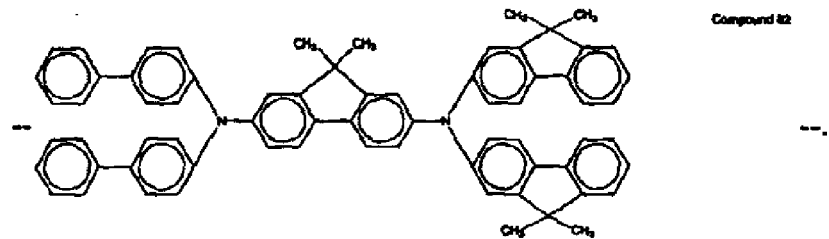

Signed and Sealed this

Seventh Day of June, 2005

JON W. DUDAS
*Director of the United States Patent and Trademark Office*